United States Patent
Vogt et al.

(10) Patent No.: US 10,722,855 B2
(45) Date of Patent: Jul. 28, 2020

(54) STORAGE AND MIXING DEVICE FOR BONE CEMENT WITH A PRESSURE PUMP

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 351 days.

(21) Appl. No.: 15/617,240

(22) Filed: Jun. 8, 2017

(65) Prior Publication Data

US 2017/0354939 A1    Dec. 14, 2017

(30) Foreign Application Priority Data

Jun. 8, 2016 (DE) .......................... 10 2016 110 564

(51) Int. Cl.
*B01F 15/00* (2006.01)
*B01F 11/00* (2006.01)
(Continued)

(52) U.S. Cl.
CPC ...... *B01F 15/0087* (2013.01); *A61B 17/8833* (2013.01); *B01F 3/1221* (2013.01);
(Continued)

(58) Field of Classification Search
CPC ................ B01F 3/1221; B01F 15/0087; B01F 15/00506; B01F 15/00974; B01F 15/0206;
(Continued)

(56) References Cited

U.S. PATENT DOCUMENTS 4,671,263 A   6/1987 Draenert
4,758,096 A   7/1988 Gunnarsson
(Continued)

FOREIGN PATENT DOCUMENTS

DE   3 640 279 A1   6/1987
DE   44 25 218 A1   1/1996
(Continued)

OTHER PUBLICATIONS

Charnley, J., "Anchorage of the Femoral Head Prosthesis of the Shaft of the Femur"; The Journal of Bone and Joint Surgery; Feb. 1960, pp. 28-30, vol. 42 B, No. 1, Manchester, England.

*Primary Examiner* — Marc C Howell
(74) *Attorney, Agent, or Firm* — Norris McLaughlin, P.A.

(57) ABSTRACT

A storage and mixing device for two-component polymethyl methacrylate bone cements having a cylindrical interior of a cartridge that is delimited on a front side by a cartridge head, a plunger arranged to be axially movable in the cylindrical interior of the cartridge and spaced from the cartridge head, a powdery first parent component of the bone cement, that is contained in the interior between the plunger and the cartridge head, a feed-through arranged in the cartridge head or in the cylinder barrel of the cartridge between the plunger and the cartridge head. The feed-through is connectable to a fluid line, a receptacle for a monomer liquid, wherein the fluid line connects the feed-through to the receptacle in a liquid-permeable manner, and a press-out device pushable into the receptacle, so that monomer liquid is pressable out of the receptacle into the fluid line. The plunger (2) is spaced from a back side of the cylindrical interior, located opposite the front side, so that, by moving the plunger in the direction of the back side, the press-out device is pushable into the receptacle and a reduced pressure is producible in the (Continued)

Figure 1:
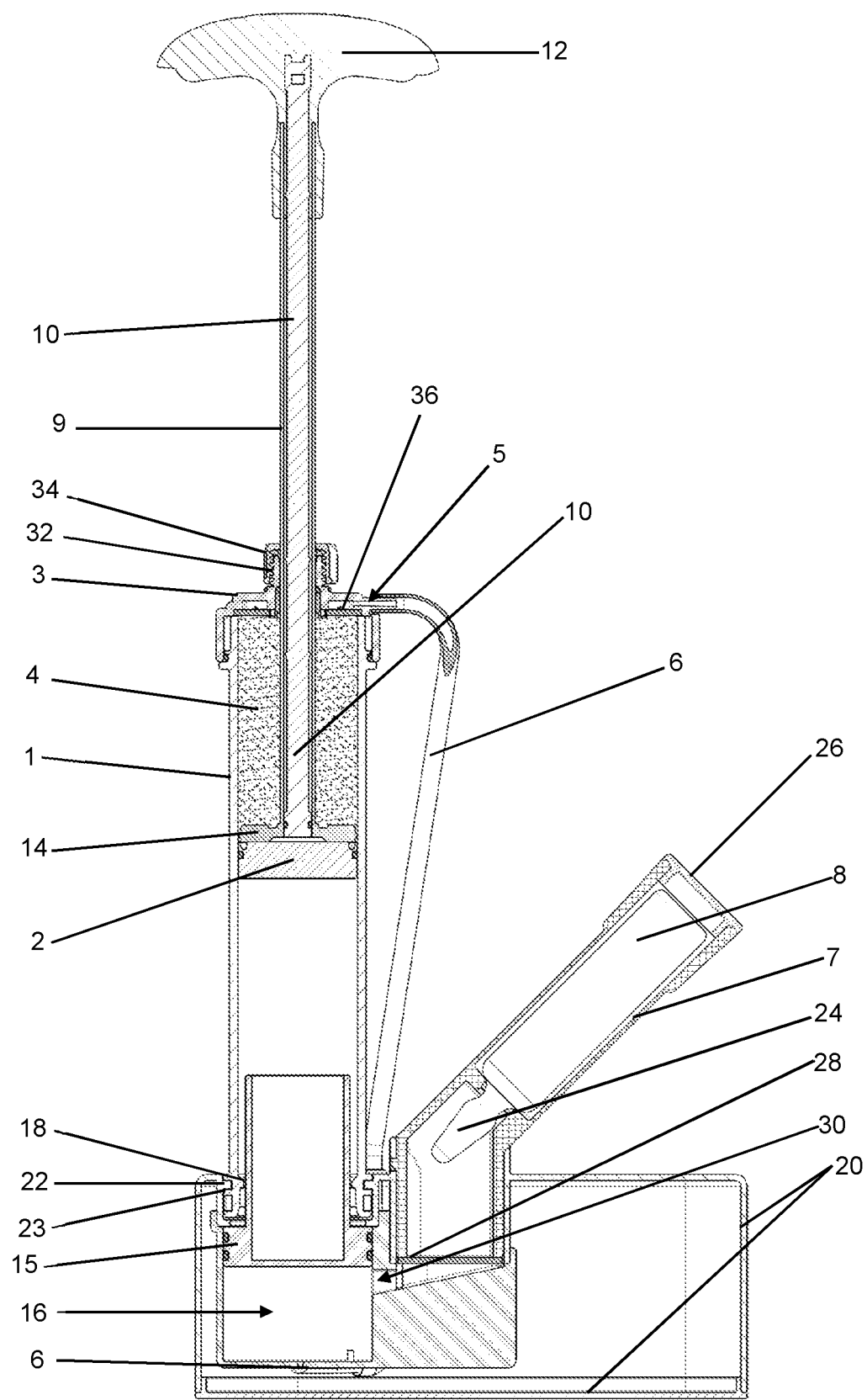

interior of the cartridge between the plunger and the cartridge head.

42 Claims, 13 Drawing Sheets

(51) Int. Cl.
    *B01F 15/02*     (2006.01)
    *A61B 17/88*     (2006.01)
    *B01F 3/12*     (2006.01)
    *B01F 3/14*     (2006.01)
    *B01F 7/00*     (2006.01)
    *B01F 7/16*     (2006.01)

(52) U.S. Cl.
    CPC ............... *B01F 3/14* (2013.01); *B01F 7/007* (2013.01); *B01F 7/161* (2013.01); *B01F 11/0054* (2013.01); *B01F 15/00506* (2013.01); *B01F 15/00974* (2013.01); *B01F 15/0206* (2013.01); *B01F 15/0237* (2013.01); *B01F 15/0258* (2013.01); *A61B 2017/8838* (2013.01); *B01F 2215/0029* (2013.01)

(58) Field of Classification Search
    CPC .............. B01F 15/0237; B01F 15/0258; B01F 2215/0029; A61B 17/8833; A61B 2017/8838
    USPC ............................................................ 366/6
    See application file for complete search history.

(56) References Cited

U.S. PATENT DOCUMENTS

| | | | |
|---|---|---|---|
| 4,973,168 A | 11/1990 | Chan | |
| 5,100,241 A | 3/1992 | Chan | |
| 5,344,232 A | 9/1994 | Nelson et al. | |
| 5,551,778 A | 9/1996 | Hauke et al. | |
| 5,586,821 A | 12/1996 | Bonitati et al. | |
| 5,588,745 A | 12/1996 | Tanaka et al. | |
| 5,624,184 A | 4/1997 | Chan | |
| 5,997,544 A | 12/1999 | Nies et al. | |
| 6,017,349 A * | 1/2000 | Heller | A61B 17/8827 366/139 |
| 6,033,105 A | 3/2000 | Barker et al. | |
| 6,709,149 B1 * | 3/2004 | Tepic | A61L 24/06 366/139 |
| 8,662,736 B2 | 3/2014 | Vogt et al. | |
| 8,757,866 B2 | 6/2014 | Vogt et al. | |
| 2008/0037365 A1 * | 2/2008 | Axelsson | B01F 13/06 366/163.1 |
| 2010/0329074 A1 * | 12/2010 | Vogt | A61B 17/8825 366/190 |
| 2014/0098629 A1 * | 4/2014 | Greter | B01F 11/0054 366/184 |

FOREIGN PATENT DOCUMENTS

| | | | |
|---|---|---|---|
| DE | 69812726 T2 | 2/2004 | |
| DE | 10 2009 031 178 B3 | 9/2010 | |
| EP | 0 692 229 A1 | 1/1996 | |
| EP | 0796653 A2 | 9/1997 | |
| EP | 1 005 901 A2 | 6/2000 | |
| EP | 1 016 452 A2 | 7/2000 | |
| EP | 1 020 167 A2 | 7/2000 | |
| EP | 1886647 A1 | 2/2008 | |
| WO | 94/26403 A1 | 11/1994 | |
| WO | 99/67015 A1 | 12/1999 | |
| WO | 00/35506 A1 | 6/2000 | |
| WO | 2012/174670 A1 | 12/2012 | |
| WO | 2014/205063 A1 | 12/2014 | |

* cited by examiner

STORAGE AND MIXING DEVICE FOR BONE CEMENT WITH A PRESSURE PUMP

This application claims foreign priority benefit under 35 U.S.C. 119 of German Application No. DE 10 2016 110 564.3 filed Jun. 8, 2016.

DESCRIPTION

The invention relates to a storage and mixing device for two-component polymethyl methacrylate bone cements, said storage and mixing device having a cartridge with a cylindrical interior.

The invention also relates to a method for mixing parent components of a bone cement, in particular of a two-component polymethyl methacrylate bone cement, using such a storing and mixing device.

Polymethyl methacrylate (PMMA) bone cements can be traced back to the fundamental work of Sir Charnley (Charnley, J.: Anchorage of the femoral head prosthesis of the shaft of the femur. J. Bone Joint Surg. 42 (1960) 28-30). PMMA bone cements consist of a liquid monomer component and a powder component. The monomer component generally contains the methyl methacrylate monomer and an activator (N,N-dimethyl-p-toluidine) dissolved therein. The powder component, also known as bone cement powder, includes one or more polymers, which are produced on the basis of methyl methacrylate and comonomers, such as styrene, methyl acrylate or similar monomers, by polymerization, preferably suspension polymerization, an X-ray-opaque material and the initiator dibenzoyl peroxide. When mixing the powder component with the monomer component, a plastically deformable paste, the actual bone cement, which is usually known as bone cement paste, is obtained as a result of the polymers of the powder component swelling in the methyl methacrylate. When mixing the powder component with the monomer component, the N,N-dimethyl-p-toluidine activator reacts with dibenzoyl peroxide, forming radicals. The radicals formed initiate the radical polymerization of methyl methacrylate. As the polymerization of methyl methacrylate continues, the viscosity of the bone cement paste increases until said paste solidifies.

The monomer most frequently used in polymethyl methacrylate bone cements is methyl methacrylate. Redox initiator systems usually consist of peroxides, accelerators and, if required, suitable reducing agents. Radicals are only formed when all elements of the redox initiator systems interact. For this reason, the elements of the redox initiator system are arranged in the separate parent components in such a manner that these cannot trigger a radical polymerization. If the composition is suitable, the parent components are storage-stable. It is only when the two parent components are mixed to form a cement paste that the elements of the redox initiator system, which were previously stored separately in the two pastes, liquids or powders, react, forming radicals which trigger the radical polymerization of the at least one monomer. The radical polymerization then leads to the formation of polymers, using the monomer, while the cement paste hardens.

PMMA bone cements can be mixed in suitable mixing receptacles with the aid of spatulas, by mixing the cement powder with the monomer liquid. Here, air bubbles can be trapped in the bone cement paste, which may negatively affect the mechanical properties of the hardened bone cement.

In order to avoid air inclusions in the bone cement paste, a plurality of vacuum cementing systems have been described, of which the following are listed as examples: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, and U.S. Pat. No. 5,344,232 A. With the vacuum cementing systems presented, it is necessary to connect an external vacuum pump in order to generate the reduced pressure. These are generally operated with compressed air using the Venturi principle. The compressed air required to operate the vacuum pumps is obtained either from stationary compressed air facilities or from electrically actuated compressors. In addition, it is also possible to use electrically actuated vacuum pumps to produce the vacuum.

A further development in cementing technology includes cementing systems in which both the cement powder and the monomer liquid are already packaged in separate compartments of the mixing systems and are only mixed together in the cementing system directly before the cement application. Such closed full-prepacked mixing systems have been proposed in EP 0 692 229 A1, DE 10 2009 031 178 B3, U.S. Pat. Nos. 5,997,544 A, 6,709,149 B1, DE 698 12 726 T2 and U.S. Pat. No. 5,588,745 A. These mixing systems require an external vacuum source too. From EP 0 796 653 A2, a device for producing bone cement from a bone cement powder and a monomer liquid in a cartridge is known, in which a vacuum is drawn by means of a connectable vacuum plunger. The disadvantage of this system is that, after a monomer liquid container has been opened or connected, monomer liquid can already penetrate into the bone cement powder and react before the remaining monomer liquid is sucked into the cartridge by means of the vacuum plunger. As a result, hardened pieces of bone cement can form in the cement paste, making it inhomogeneous, which complicates applicability of the bone cement paste and negatively affects the mechanical properties of the hardened bone cement. In addition, the use of the device is relatively complex and therefore prone to error due to the numerous steps involved in connecting the parts of the device and producing the vacuum.

The U.S. Pat. No. 8,757,866 B2 discloses a storage and mixing device as a full-prepacked mixing system, in which the parent components required for producing the bone cement paste are already stored in the storage and mixing device and can be combined and mixed in the storage and mixing device. The storage and mixing device has a two-piece delivery plunger for closing a cement cartridge. Here, a combination of a gas-permeable sterilization plunger and a gas-impermeable sealing plunger is used. This principle of a closed vacuum mixing system is realized in the closed PALACOS® PRO cementing system, which is produced and distributed by Heraeus Medical GmbH.

WO 00/35506 A1 proposes a device in which polymethyl methacrylate bone cement powder is stored in a cartridge, wherein the cement powder fills the entire volume of the cartridge and the intermediate spaces between the particles of the cement powder have a volume that corresponds to the volume of the monomer liquid required for producing bone cement paste with the cement powder stored in the cartridge. This device is structured in such a manner that a vacuum causes the monomer liquid to be introduced into the cartridge from above, wherein, for this purpose, a vacuum is applied at a vacuum port on the underside of the cartridge. As a result, the monomer liquid is drawn through the cement powder while the air located in the intermediate spaces of the cement particles is displaced by the monomer liquid. Here, the cement paste formed is not mechanically mixed with a stirrer.

The disadvantage of this system is that cement powders which swell quickly with the monomer liquid cannot be mixed with this device, as the quickly swelling cement powder particles form a gel-type barrier after the monomer liquid has penetrated into the cement powder up to approximately 1 to 2 cm and hinder the migration of the monomer liquid through the entire cement powder. Further, the possibility cannot be excluded that a vacuum causes the monomer liquid to be sucked off via the vacuum port after the monomer liquid has completely penetrated the cement powder. Then, insufficient monomer liquid is available for hardening by radical polymerization, or the mixing ratio, and therefore also the consistency of the bone cement, is inadvertently altered. Further, it is a problem that the air trapped between the cement powder particles is to be displaced from above downwards by the monomer liquid, as the air, which is specifically lighter than the monomer liquid, has the desire to wander upwards in the cement powder due to gravity, rather than migrating downwards in the direction of the vacuum port.

When vacuum mixing systems are used for cementing, external vacuum pumps must be provided. These vacuum pumps are expensive and must be cleaned after use. Further, vacuum hoses are required to connect the vacuum pumps to the vacuum mixing systems. These vacuum hoses must be provided with the vacuum mixing systems. Before mixing with a vacuum mixing system, the vacuum pump must therefore first be assembled in the operating theater (OP theater) and connected to an energy source, such as compressed air or electric power. The vacuum pump is then connected to the vacuum mixing system by means of a vacuum hose. These assembly steps cost valuable OP time and are open to possible error. The vacuum pump and the connecting lines to the vacuum mixing system and to external energy sources and supply lines require space and present potential stumbling hazards and obstacles, which may interfere with the occasionally hectic procedure during an operation.

An interesting concept is proposed by EP 1 886 647 A1. Here, the cement powder is stored in an evacuated cartridge and the monomer liquid is located in a separate container. When the cartridge, which is under reduced pressure, is opened, the monomer liquid is sucked into the cartridge without air flowing in. A bone cement paste is produced which is free of air inclusions. This concept requires that the cartridge remains closed to be vacuum-tight during storage before use, and no non-sterile air can enter. For this purpose, the cartridge must be hermetically sealed in a stable manner. The disadvantage is therefore that the structure is complex and that the contents of the cartridge cannot be mixed by means of a mixing system to be operated externally after the monomer liquid has been sucked in, as a feed-through for a mixing rod or a mixing tube cannot easily be rendered permanently vacuum-tight.

The object of the invention is therefore to overcome the disadvantages of the prior art. In particular, the disadvantages of the known vacuum mixing systems with an external vacuum source are to be overcome. Here, the invention has the object, among others, to develop a simple closed storage and mixing device in which polymethyl methacrylate bone cement powder (cement powder) and monomer liquid are stored in separate compartments and can then be mixed. The medical user should be able to combine and mix the polymethyl methacrylate bone cement powder with the monomer liquid within the storage and mixing device without the two parent components coming into contact with the medical user. Any contact of the medical user with the polymethyl methacrylate bone cement powder and with the monomer liquid should be excluded as far as possible. The device to be developed is preferably a full-prepacked mixing system. The storage and mixing device should be designed in such a manner that the monomer liquid can be transferred into the polymethyl methacrylate bone cement powder without the use of external vacuum pumps which are actuated by compressed air or compressors. It is further important that the storage and mixing device ensures, in a functional and reliable manner, the production of bone cement paste without external energy sources, such as compressed air, vacuum or electric power, even under the simplest external conditions. The storage and mixing device should be usable autonomously without additional technical equipment. Also, the storage and mixing device should be structured as simply and inexpensively as possible.

The storage and mixing device should be simplified such that, with just one manual operating element, a monomer liquid container or a glass ampoule or a foil bag as a monomer liquid container can first be opened, and then, without using an externally produced vacuum, a transfer of the monomer liquid into the cartridge with the cement powder contained therein can be performed manually. Faulty operation should be precluded as far as possible by the construction.

A method should further be provided, which enables a monomer liquid transfer and mixing in full-prepacked mixing systems, and in which, after the monomer liquid container has been opened, only a single operating element must be operated to transfer the monomer liquid, produce a reduced pressure in the mixing chamber (the cartridge) and mix with the bone cement powder to form the desired bone cement paste. Here, it should be possible to produce the storage and mixing device to be developed mainly from inexpensive plastic.

Further, a storage and mixing device which can be produced at low cost and which functions reliably for mixing a medical bone cement and for storing the parent components of the bone cement as well as a method for mixing the bone cement should be found, in which the simplest possible manual operation for mixing the parent components can be used, as far as possible without the necessity of using an external or additional energy source and without air inclusions being formed in the mixed product.

The first parent component of the polymethyl methacrylate bone cement as a mixed product should be a powder or bone cement powder, and the second parent component should be present in the form of a liquid, the monomer liquid. It should preferably be possible to store the two parent components of the bone cement separately in the full-prepacked mixing system and to securely combine them using the storage and mixing device.

The objects of the invention are achieved by a storage and mixing device for two-component polymethyl methacrylate bone cements, said storage and mixing device having
a) a cartridge with a cylindrical interior, wherein the cylindrical interior is delimited on a front side by a cartridge head with a closed delivery opening,
b) a plunger which is arranged to be axially movable in the cylindrical interior of the cartridge and which is spaced from the cartridge head, wherein the plunger circumferentially rests against the inner wall of the interior, so that the plunger divides the interior of the cartridge into two sections, c) a powdery first parent component of the bone cement, which is contained in the interior between the plunger and the cartridge head, d) a feed-through which is arranged in the cartridge head or in the cylinder barrel of the cartridge between the plunger and the cartridge head, wherein the feed-through is connected to a fluid line, e) a receptacle for a monomer liquid, wherein the fluid line connects the feed-through to the receptacle in a liquid-permeable manner, wherein the monomer liquid as a second parent component of the bone cement is contained in the receptacle or is fillable or introducible into the receptacle, f) a press-out device which is pushable into the receptacle, so that monomer liquid is pressable out of the receptacle into the fluid line, g) wherein the plunger is spaced from a back side of the cylindrical interior, located opposite the front side, so that, by moving the plunger in the direction of the back side, the press-out device is pushable into the receptacle and a reduced pressure is producible in the interior of the cartridge between the plunger and the cartridge head.

When the reduced pressure has been produced in the interior of the cartridge between the plunger and the cartridge head due to said movement of the plunger, this reduced pressure is passed through the feed-through and into the fluid line.

Preferably, a pump plunger is used as the press-out device. An elastic membrane can also be used as the press-out device, wherein the elastic membrane expands into the receptacle (thus moving into the receptacle or being pushed into the receptacle according to the present invention), pressing the monomer liquid out of the receptacle into the fluid line as a result.

Preferably, no further structural element is provided between the plunger and the powdery first parent component.

It can preferably be provided that the first parent component is a cement powder.

Further, it can preferably be provided that the plunger divides the interior of the cartridge into two sections in a gas-tight manner. This can ensure that movement of the plunger in the direction of the back side enables a reduced pressure to be produced in the interior of the cartridge and to be maintained at least until the end of the mixing process.

The interior of the cartridge has a cylindrical geometry. The cylindrical shape is the simplest with which the interior of the cartridge can be realized. In geometric terms, a cylindrical shape is the shape of a general cylinder with any base area, i.e. not only a cylinder with a circular base. The delimiting inner wall of the interior can therefore be a cylinder with any base, and the cylinder barrel of the cartridge, if present, can also be a cylinder with any base, i.e. also with a non-circular or non-round base. According to the invention, however, a cylindrical geometry with a rotationally symmetrical and in particular a circular base is preferred for the interior of the first cartridge as these are easiest to produce and it is less easy for the plunger to get stuck in the interior when it is axially moved in the interior. In addition, there is less probability of possible leaks between the inner wall of the interior and the plunger during movement of the plunger.

The fact that the plunger is axially movable in the cylindrical interior of the cartridge means that the plunger is axially movable along the cylinder axis of the cylindrical interior.

According to the invention, it can be provided that the plunger is a delivery plunger by means of which the mixed bone cement paste is pressable out of the cartridge through the delivery opening or through the delivery pipe or the hollow mixing rod by advancing the delivery plunger in the direction of the cartridge head.

The back side of the interior is also the back side of the cartridge.

In storage and mixing device according to the invention it can be provided that the plunger in the interior of the cartridge is pushable or pullable manually in the direction of the back side of the interior by means of a rod or another force transmission means, wherein preferably an actuating means or a handle for operating the rod or the force transmission means is affixed to the rod or the force transmission means.

In this way, the reduced pressure can be produced manually in a simple and direct manner and the press-out device and therefore the monomer liquid can be actuated manually in a simple manner, which reduces the risk of possible malfunctions on the one hand and avoids complex and expensive structural elements, such as motors, energy stores or controls, on the other. In addition, this can ensure simple and safe operability of the storage and mixing device.

It can further be provided that a filter, in particular a porous filter, is arranged in the cartridge head, in the feed-through and/or in the fluid line, wherein the filter is permeable to the monomer liquid and impermeable to the powdery first parent component.

This prevents cement powder or the powdery first parent component from making its way into the fluid line as far as the monomer liquid, prematurely reacting there with the monomer liquid, solidifying or gelling, and blocking the fluid line as a result. For this purpose, the filter is preferably arranged in the cartridge head, in the feed-through or in the fluid line in the region of the feed-through.

Preferably, it can also be provided that the plunger is spaced from a back side of the cylindrical interior, located opposite the front side, to an extent that the reduced pressure is able to suck the monomer liquid out of the fluid line into the interior of the cartridge.

In this way, the stroke of the plunger is also sufficient to suck the monomer liquid through the fluid line into the interior of the cartridge with the aid of the reduced pressure produced in the interior of the cartridge, in addition to the transport caused by movement of the press-out device into the receptacle.

For this purpose, it can further be provided that the plunger is spaced from the back side of the cylindrical interior such (or to an extent) that the space for displacement of the plunger to reach the back side is at least equal to the volume of the monomer liquid to be sucked in, preferably at least equal to the volume of the fluid line and the receptacle.

A further development of the present invention proposes that the storage and mixing device has a container which is separate from the cartridge and from the receptacle and in which the monomer liquid is contained, wherein the container is connected to the receptacle, in particular via an opening, wherein preferably a closed glass ampoule or a foil bag containing the monomer liquid is arranged or is arrangeable in the container, wherein the glass ampoule is breakable open within the container or the foil bag is pierceable open or tearable open within the container.

In this way, a so-called full-prepacked mixing system is provided in which all parent components, i.e. the two parent components (cement powder as the first powdery parent component and monomer liquid as the second parent component), are already contained in the storage and mixing device, can also be stored therein for longer periods and are mixable within the storage and mixing device.

In such storage and mixing devices it can be provided that the cartridge, the receptacle, the separate container and the fluid line are connected to a common stand, wherein the receptacle, the container and the fluid line are permanently connected to the stand and the cartridge is releasably connected to the stand, the cartridge preferably being screwed to the stand by means of a thread or connected to the stand by means of a latching mechanism.

This simplifies the use of the storage and mixing device. In operation theaters, a planar surface, such as a table, is present in most cases, so that the storage and mixing device can be installed and used there with the aid of the stand, without a need to hold the storage and mixing device in the hand. This simplifies the use of the storage and mixing device even further.

It can further be provided that a monomer liquid container, in particular a foil bag or a glass ampoule, is contained in the separate container and is openable within the separate container, so that the monomer liquid flows out of the opened monomer liquid container into the receptacle, wherein preferably an opening device for opening the monomer liquid container, which is operable from outside, is arranged on the container.

In this way, a so-called full-prepacked mixing system is provided in which all parent components, i.e. the two parent components (cement powder as the first powdery parent component and monomer liquid as the second parent component), are already contained in the storage and mixing device, are storable therein and are mixable within the storage and mixing device. The glass ampoule or the foil bag, which is preferably coated with aluminum, are particularly suitable for long-term storage of the monomer liquid as the second parent component for producing the PMMA bone cement paste. This simplifies and facilitates the use of the storage and mixing device.

In order for the monomer liquid to be able to flow into the receptacle without the influence of additional force at first, the storage and mixing device must be correctly installed, so that gravity produces the desired direction of flow. Accordingly, the terms "at the top" and "at the bottom" used within the context of the present invention, as well as "above" and "below" are always in relation to the correct installation of the storage and mixing device.

A monomer liquid container with several chambers for storing the monomer liquid can also be used. Within the context of the present invention, a monomer liquid container is therefore also understood as being a plurality of separate, individual partial monomer liquid containers which are introducible into the separate container and are openable by means of the opening device.

It can be provided that a screen or a filter is arranged in the line leading to the receptacle or also in or on the fluid line to the cartridge, with which fragments or scraps of the opened monomer liquid container can be retained. The screen or filter is preferably located in the container, directly below the monomer liquid container.

A further development of the invention relating to the use of gravity as an actuating means for the flow of monomer liquid into the fluid line proposes that the separate container for the monomer liquid container is arranged above the receptacle. As a result, the monomer liquid can flow out of the monomer liquid container, downwards into the receptacle, due to gravity, after the monomer liquid container has been opened.

According to a preferred further development of the invention it can be provided that a mixing device is arranged in the interior of the cartridge between the plunger and the cartridge head, by means of which the first parent component is mixable with the monomer liquid in the interior of the cartridge.

In this way, the first parent component can be well mixed with the monomer liquid in the interior of the cartridge in order to produce a bone cement paste which is as homogeneous as possible. The mixing device can preferably be operated manually from outside.

Here, it can be provided that the mixing device is operable from outside the cartridge by means of a mixing rod, wherein the mixing rod passes through the cartridge head in a gas-tight manner and is rotatable and movable in the axial direction, the mixing rod preferably passing through the delivery opening.

In this way, the mixing device can be operated manually from outside the storage and mixing device in a simple and powerful manner. In addition, the user can make a good estimation of the consistency of the bone cement paste and therefore the usability of the bone cement paste, based on the resistance against movement of the mixing device.

According to the invention, it can be provided that a fastening means, in particular an outer thread, is provided in the region of the cartridge head on the outside of the cartridge. A separate delivery pipe is affixable thereto. Preferably however, a hollow tubular mixing rod is used, by means of which the mixing device is operable and the plunger in the interior is pushable in the direction of the back side of the interior in order to produce the reduced pressure in the interior, wherein the tubular mixing rod can be used as a delivery pipe after a closure has been removed from the tubular mixing rod. In this case, an outer thread is not required any more, although the outer thread can also be used to affix the cartridge in a delivery device or press-out device for advancement of the plunger in the direction of the cartridge head in order to press out and apply the ready-mixed bone cement paste. To close the delivery opening, an extractable core is arranged within the hollow mixing rod, which closes the tubular mixing rod to the outside.

It can further be provided that the plunger is pushable in the direction of the back side of the interior of the cartridge by means of the mixing rod.

In this way, the plunger can be actuated by means of the same device which is used for actuating the mixing device, namely the mixing rod, in order to push the press-out device into the receptacle and to produce the reduced pressure in the interior of the cartridge. As a result, only one common device is required for both or all three functions, and the storage and mixing device requires only one feed-through that must be sealed to serve both or all three purposes.

It can further be provided that the mixing rod is a delivery pipe in which a manually removable core is arranged, so that the mixed bone cement paste is dischargeable from the interior of the cartridge through the delivery pipe without the core.

For this purpose, the delivery pipe is pulled out of the interior of the cartridge as far as a stop, preferably in advance. If the mixing rod is used as a delivery pipe, no additional or separate delivery pipe is required which would have to be affixed to the storage and mixing device. The mixing rod is guided in or passes through the delivery opening for this purpose while being sealed against the cartridge head and being axially movable and rotatable.

Alternatively it can be provided that the storage and mixing device has a separate delivery pipe with a static mixer, which is affixable to the cartridge, preferably to the fastening means on the cartridge, wherein particularly preferably an inner thread matching the outer thread on the cartridge is provided on the delivery pipe and/or elements of a bayonet mount and/or latching elements of a latching mechanism are provided.

The present invention also proposes that inside the interior of the cartridge, on the back side, a stop is provided which limits the movement of the plunger in the direction of the back side.

This prevents the plunger from being able to be displaced beyond the back side of the interior and bone cement paste from inadvertently passing to the outside.

It can also be provided that the plunger has at least one latching element which is releasably engageable with a complementary latching element on the inner side of the cartridge in the region of the back side of the interior.

In this way, the plunger is held in position when it has been moved as far as the back side. This prevents inadvertent movement of the plunger while mixing the contents of the interior and movement of the plunger beyond the latching position. To deliver the ready-mixed bone cement paste, the latching mechanism can be easily released.

In storage and mixing devices according to the invention it can be provided that the cartridge, the receptacle, the cartridge head and the plunger, preferably also a pump plunger as a press-out device, are made of plastic, wherein preferred plastics are polyethylene-co-vinyl alcohol (EVOH), polybutylene terephthalate (PBT), polyethylene terephthalate (PET) and polymethacrylic acid methyl ester co-acrylonitrile.

Preferred storage and mixing devices can also be characterized in that a gas-permeable opening, in particular a closable gas-permeable opening, is arranged in the cartridge head, wherein a porous disc which is permeable to gases and impermeable to solid particles is arranged between the first parent component and the opening, wherein the porous disc is preferably arranged in the cartridge head.

In this way, a sterilization of the storage and mixing device can also be performed in the interior of the cartridge with the aid of a sterilizing gas, such as ethylene oxide. The opening is preferably arranged next to the delivery opening and is closable by means of a closure.

It can be provided that an opening is arranged in the cartridge head, above the porous disc, which opening is closable to be gas-tight and has an area of at least 20 $mm^2$ and is connected to the surrounding atmosphere.

According to the invention, it can be provided that the plunger is a delivery plunger by means of which the mixed bone cement paste is pressable out of the cartridge through the delivery opening or through the delivery pipe or the hollow mixing rod by advancing the delivery plunger in the direction of the cartridge head.

Preferably, the cartridge head is arranged at the top and the back side of the cartridge is arranged at the bottom when the storage and mixing device is installed correctly. Further, the receptacle is preferably arranged below the feed-through or arranged at a lower height than the feed-through. In this way, the monomer liquid is prevented from being able to flow into the cartridge inadvertently, i.e. without actuating the plunger in the direction of the back side of the cartridge.

It can preferably also be provided that a mouth for introducing the monomer liquid into the receptacle is arranged in the region of the press-out device, wherein the mouth is closed by pushing in the press-out device when the press-out device begins to move into the receptacle.

This ensures that the press-out device presses the monomer liquid contained in the receptacle into the fluid line, rather than through the mouth.

According to a first preferred embodiment it can be provided, according to the invention, that the receptacle is arranged on the back side of the cartridge and the plunger pushes the press-out device into the receptacle during movement in the direction of the back side of the cartridge, wherein the region between the press-out device and the plunger is preferably opened towards the outside.

In this way, the press-out device can be mechanically actuated by the plunger, whereby a particularly high force can act on the press-out device, enabling the monomer liquid to be pressed out of the receptacle through the fluid line into the interior of the cartridge with high pressure. The fact that the region between the plunger and the press-out device is open ensures that trapped air can escape, thus preventing the area from acting as a gas spring which inadvertently moves the plunger back in the direction of the cartridge head when there is less or no pressure on the press-out device.

In this embodiment it can also be provided that the plunger is spaced from the press-out device, so that a reduced pressure is first built up in the interior of the cartridge, without the press-out device being moved, when the plunger is moved in the direction of the back side of the cartridge in a first section, and, in addition, the press-out device is pushed into the receptacle when the plunger is moved in a second section.

This ensures that the gas in the interior of the cartridge is first depleted and can escape between the powder particles of the first parent component before the monomer liquid flows into the interior of the cartridge or is pressed into the interior of the cartridge.

It can further be provided that the press-out device is a pump plunger and the receptacle is a hollow cylinder in which the pump plunger is axially movable, wherein an extension, in particular in the form of a cylindrical body, is arranged on the upper side of the pump plunger, which extension has an outer diameter smaller than or equal to the inner diameter of the interior of the cartridge, wherein the pump plunger with the extension is arranged in the hollow cylinder in such a manner that the extension projects into the interior of the cartridge.

In this way, the pump plunger can be actuated by the plunger in a simple manner, in that the plunger, moving in the interior of the cartridge, exerts pressure on the extension of the pump plunger, thus advancing it in the hollow cylinder. As a result, the monomer liquid is pressed out of the hollow cylinder and into the cartridge through the fluid line. The plunger as such can be used later as a delivery plunger for pressing out the mixed bone cement paste as no attachment is located on the plunger but the attachment is mounted to the pump plunger.

According to a second preferred alternative embodiment it can be provided, according to the invention, that the receptacle is delimited by a closed hollow cylinder which is separate from the cartridge and in which a pump plunger as a press-out device is supported to be axially movable, wherein the pump plunger is in circumferential and tight contact with the inner wall of the hollow cylinder, wherein the hollow cylinder is connected to the fluid line at a first, preferably lower, base and connected to the interior of the cartridge via a compressed gas line or a hydraulic line on the back side of the cartridge at a second, preferably upper, base, wherein the back side of the cartridge is closed except for the mouth leading into the compressed gas line or the hydraulic line, so that, during movement of the plunger in the direction of the back side of the interior, an overpressure or a pressure is produced in the space between the plunger and the back side, which is passed into the hollow cylinder through the compressed gas line or the hydraulic line.

In this way, the pump plunger in the hollow cylinder can be actuated with the aid of the overpressure or pressure produced by movement of the piston and exerted on a hydraulic fluid in the space between the plunger and the back side of the cartridge. For this purpose, the pump plunger preferably rests against the first (upper) base of the hollow cylinder and/or is spaced from the second (lower) base of the hollow cylinder. The hollow cylinder is preferably permanently connected to a foot part.

The objects addressed by the present invention are also achieved by a method for mixing the parent components of a bone cement, in particular a two-component polymethyl methacrylate bone cement, using a storage and mixing device according to the invention, characterized by the following steps:

a) the plunger is moved in the direction of the back side of the cylindrical interior of the cartridge, wherein a reduced pressure is produced in the interior of the cartridge between the plunger and the cartridge head due to said movement of the plunger,
b) the press-out device is pushed into the receptacle due to said movement of the plunger, whereby a monomer liquid contained in the receptacle is pressed into the interior of the cartridge through the fluid line due to said movement of the press-out device,
c) the monomer liquid and the first parent component are mixed to form the bone cement paste in the interior of the cartridge, and
d) the bone cement paste is discharged from the interior of the cartridge by advancing the plunger in the direction of the cartridge head.

Steps a) and b) can, at least at times, be performed simultaneously, while steps c) and d) are performed chronologically after each other and also chronologically after steps a) and b). Steps a) and b) can, at least at times, be performed simultaneously as the press-out device is actuated in the receptacle at times or throughout the entire movement of the plunger.

Here, it can be provided that the monomer liquid is sucked out of the fluid line into the interior of the cartridge by the reduced pressure in the interior of the cartridge.

In this way, the reduced pressure produced in the cartridge is also used to move the monomer liquid out of the receptacle, in addition to the pressure exerted by the press-out device. The reduced pressure in the interior of the cartridge is already built up during movement of the plunger, and this reduced pressure can already cause the monomer liquid to be sucked into the interior of the cartridge.

It can further be provided that the monomer liquid is introduced into the receptacle before step a), in particular after a monomer liquid container has been opened in a container of the storage and mixing device.

In this way, the method becomes usable for full-prepacked systems as the monomer liquid can also be stored in the storage and mixing device, in a dedicated monomer liquid container, such as a glass ampoule or a metallized foil bag, for longer periods.

It can further be provided that, in step a), the plunger is pushed in the direction of the back side of the cartridge by means of a mixing rod, wherein the mixing rod is movably supported in a gas-tight feed-through, in particular in the delivery opening, in the cartridge head, and, in step c), the monomer liquid is mixed with the first parent component by moving a mixing device, which is connected to the mixing rod, in the interior of the cartridge between the plunger and the cartridge head, by moving the mixing rod and therefore the mixing device.

In this way, the mixing rod, which is present for moving the mixing device in the interior of the cartridge, is also used for moving the plunger and hence for moving the press-out device and producing the reduced pressure in the interior of the cartridge. Particularly preferably, this mixing rod can be designed as a tube and therefore also be used as a delivery pipe for applying the mixed bone cement paste.

Here, it can again be provided that the mixing device is pulled towards the cartridge head by means of the mixing rod and a core is removed from the mixing rod between steps c) and d), so that the mixing rod without the core forms a delivery pipe through which the mixed bone cement paste is pressed out of the interior of the cartridge in step d).

In this way, the mixing rod becomes also usable as a delivery pipe, and the delivery opening is usable to pass the mixing rod therethrough.

A further development of the method according to the invention can provide that, before step d), the cartridge is separated from the storage and mixing device and is inserted into a press-out device by means of which the plunger is pushed in the direction of the cartridge head in step d), using a tappet or an advanceable rod, in order to discharge the bone cement paste from the interior of the cartridge.

In this way, the cartridge can be used separately from the storage and mixing device in order to apply the ready-mixed bone cement paste. This facilitates handling during application.

It can further be provided that the receptacle is a hollow cylinder and the press-out device is a pump plunger which is arranged to be movable in the longitudinal direction in the hollow cylinder, wherein the pump plunger is moved in the hollow cylinder by exerting pressure with the plunger or is moved pneumatically or hydraulically by means of an overpressure or pressure produced in the interior between the back side of the cartridge and the plunger, wherein preferably the overpressure is passed into the hollow cylinder through a compressed gas line or the pressure is passed into the hollow cylinder through a hydraulic line.

In this way, the force required to move the pump plunger is obtained from movement of the plunger in the cartridge in a simple manner. This means it is sufficient to actuate the plunger in order to perform a plurality of different processes in the storage and mixing device.

It can also be provided that a monomer liquid container, in particular the glass ampoule or the foil bag, is opened in the storage and mixing device before steps a) and b), wherein the monomer liquid flows out of the monomer liquid container and flows into the receptacle, preferably flows into the receptacle through a screen and/or a filter.

According to the invention, it can also be provided that the cartridge head is closed to be gas-tight before step a). This ensures that a reduced pressure is producible in the interior of the cartridge, under which the parent components can be mixed and which can also be used to suck in the monomer liquid, if required. At the same time, however, the interior of the cartridge can first be sterilized with the aid of a sterilizing gas, such as ethylene oxide, through the opened cartridge head.

Storage and mixing devices according to the invention and methods according to the invention can, in theory, also be realized using a plurality of cartridges in each of which a movable plunger is arranged. Such solutions are understood as being within the scope of the present invention as, here too, just one cartridge is operated or is operatable individually according to the invention.

The invention is based on the surprising recognition that the plunger, which is also used to deliver the mixed bone cement paste from the cartridge, can first be used to actuate a press-out device by means of which a monomer liquid can be pressed out of a receptacle into the interior of the cartridge where it is to be mixed with the bone cement. Further, it has surprisingly been found that the same plunger can be used to produce a reduced pressure and therefore to suck in the monomer liquid. If the mixing rod is also used to operate or move the plunger in order to produce the reduced pressure, additional structural elements can be avoided here. Further, the mixing rod can also be used as a delivery pipe in order to minimize the number of structural elements required. Here, the idea is that the plunger at first does not rest against the back side of the interior of the cartridge but is spaced from it. The stroke of the plunger to reach the back side of the interior of the cartridge can then be used to actuate the press-out device by means of which the monomer liquid can be pressed into the interior of the cartridge and to produce a reduced pressure in the interior of the cartridge, which can be used to mix a bone cement with no or few bubbles and by which the monomer liquid can be sucked into the interior of the cartridge. The remaining reduced pressure can therefore be used to mix the parent components together under reduced pressure, so that as few gas or air inclusions as possible will form in the bone cement paste being produced.

A first storage and mixing device for polymethyl methacrylate bone cement according to the invention is, for example, composed of
a) a cylindrical cartridge,
b) a plunger which is axially movable in the cylindrical cartridge,
c) a cartridge head with a feed-through for a mixing rod,
d) a mixing rod which is axially displaceable through the feed-through of the cartridge head,
e) a mixing device which is connected to the end of the mixing rod arranged in the interior of the cartridge,
f) an actuating means which is arranged at the outer end of the mixing rod,
g) at least one monomer liquid container arranged outside the cartridge,
h) an opening device for the monomer liquid container,
i) wherein the at least one monomer liquid container is connected to a hollow cylinder in a liquid-permeable manner by an opening, wherein the monomer liquid container is arranged above the opening,
j) a fluid line which, at a closed base of the hollow cylinder, provides a liquid-permeable connection of the hollow cylinder with the cavity formed by the cartridge, the cartridge head and the plunger,
k) a cement powder which is arranged in the cavity formed by the cartridge, the cartridge head and the plunger,
l) wherein the hollow cylinder is closed by a lid on the upper side, which lid is connected in a gas-permeable manner to a cartridge holder by means of a compressed gas line,
m) wherein an axially movable pump plunger is arranged in the hollow cylinder above the opening in the hollow cylinder and wherein the cartridge is connected to the cartridge holder in a releasable and gas-tight manner.

Another alternative storage and mixing device for polymethyl methacrylate bone cement according to the invention is, for example, composed of a) a cylindrical cartridge,
b) a plunger which is axially movable in the cylindrical cartridge,
c) a cartridge head with a feed-through for a mixing rod,
d) a mixing rod which is axially displaceable through the feed-through of the cartridge head,
e) a mixing device which is connected to the end of the mixing rod arranged in the interior of the cartridge,
f) an actuating means which is arranged at the outer end of the mixing rod,
g) at least one monomer liquid container arranged outside the cartridge,
h) an opening device for the monomer liquid container,
i) a cement powder which is arranged in the cavity formed by the cartridge, the cartridge head and the plunger,
j) wherein an annular cartridge holder is arranged below the cartridge, in a foot part, wherein the cartridge is releasably connected to the cartridge holder,
k) a hollow cylinder which is arranged below the cartridge holder, wherein the at least one monomer liquid container is connected to the hollow cylinder in a liquid-permeable manner by an opening and wherein the monomer liquid container is arranged above the opening,
l) wherein the hollow cylinder is closed by a base on the lower side, which bottom is connected to the fluid line in a liquid-permeable manner,
m) wherein an axially movable pump plunger is arranged in the hollow cylinder above the opening in the hollow cylinder, and
n) wherein a cylindrical body is arranged on the upper side of the pump plunger, which body has an outer diameter smaller than or equal to the inner diameter of the cartridge, wherein the pump plunger with the cylindrical body is arranged in the hollow cylinder in such a manner that the upper end of the cylindrical body projects into the interior of the cartridge.

Here, it can preferably be provided that the plunger is axially arranged in the cartridge in such a manner that the space for displacement formed by the cartridge, the cartridge base and the plunger has a volume equal to or larger than the total volume of the fluid line and the at least one monomer liquid container.

The feed-through for the mixing rod is realized by the delivery opening, or is called such herein when the mixing rod is used as a delivery pipe. The actuating means can, for example, be a handle by means of which the mixing rod is manually operable.

According to the invention, a foot part can be provided here, to which the cartridge is releasably connected and which is permanently connected to the at least one monomer liquid container.

It can further be provided that a porous disc is arranged in the cartridge head, which disc is permeable to gases and liquids and is connected to a gas-permeable feed-through and closes the cavity, allowing gases and liquids and not allowing solid particles to pass.

An opening can be arranged in the cartridge head, above the porous disc, which opening is closable to be gas-tight and has an area of at least 20 mm$^2$ and is connected to the surrounding atmosphere.

According to the invention, it can further be provided that the plunger has at least one latching element which can be releasably engaged with a complementary latching element on the inner side of the cartridge above the cartridge base.

The invention includes, for example, a method for mixing and delivering polymethyl methacrylate bone cement. Said method is characterized by the following sequential steps:
a) closing the cartridge head to be gas-tight,
b) opening the at least one monomer liquid container,
c) flowing of the monomer liquid out of the monomer liquid container into the hollow cylinder through the opening,
d) pushing the actuating means of the mixing rod in the direction of the cartridge base (back side of the interior of the cartridge),
e) displacing the plunger in the direction of the cartridge base by means of the mixing rod,
f) producing a reduced pressure in the cavity (in the interior of the cartridge) formed by the cartridge, the cartridge head and the plunger,
g) producing an overpressure in the cavity (in the interior of the cartridge) formed by the cartridge, the closed back side of the cartridge and the plunger,
h) passing the overpressure into the hollow cylinder above the axially displaceable pump plunger through a pressure line,
i) moving the pump plunger in the direction of the base of the hollow cylinder,
j) transferring the monomer liquid from the hollow cylinder into the interior of the cartridge through the fluid line due to the reduced pressure produced and by pressing it out of the hollow cylinder by the pump plunger being moved in the direction of the base,
k) mixing the cement powder with the monomer liquid by manually actuating the actuating element of the mixing rod by axial and rotating movement of the mixing device,
l) pulling the mixing rod towards the cartridge head,
m) removing a core from the hollow mixing rod,
n) inserting the cartridge into a press-out device,
o) actuating the press-out device, wherein the plunger is moved in the direction of the cartridge head, and
p) pressing the mixed bone cement paste out of the cartridge through the hollow mixing rod.

The method is designed to make use of the aforesaid first storage and mixing device according to the invention and reflects its way of operation.

The invention also includes, for example, an alternative method for mixing and delivering polymethyl methacrylate bone cement. Said alternative method is characterized by the following sequential steps:
a) closing the cartridge head to be gas-tight,
b) opening the at least one monomer liquid container,
c) flowing of the monomer liquid out of the monomer liquid container into the hollow cylinder through the opening,
d) pushing the actuating means of the mixing rod in the direction of the cartridge base (back side of the interior of the cartridge),
e) displacing the plunger in the direction of the cartridge base by means of the mixing rod,
f) producing a reduced pressure in the cavity (in the interior of the cartridge) formed by the cartridge, the cartridge head and the plunger,
g) displacing the cylindrical body of the pump plunger by axially displacing the plunger in the direction of the back side of the cartridge,
h) transferring the monomer liquid from the hollow cylinder into the interior of the cartridge through the fluid line by means of the reduced pressure produced and by pressing it out of the hollow cylinder by the pump plunger being moved in the direction of the base,
i) mixing the cement powder with the monomer liquid by manually actuating the actuating element of the mixing rod by axial and rotating movement of the mixing device,
j) pulling the mixing rod towards the cartridge head,
k) removing a core from the hollow mixing rod,
l) inserting the cartridge into a press-out device,
m) actuating the press-out device, wherein the plunger is moved in the direction of the cartridge head, and
n) pressing the mixed bone cement paste out of the cartridge through the hollow mixing rod.

The alternative method is designed to make use of the aforesaid further, alternative storage and mixing device according to the invention and reflects its way of operation.

Figure 2:
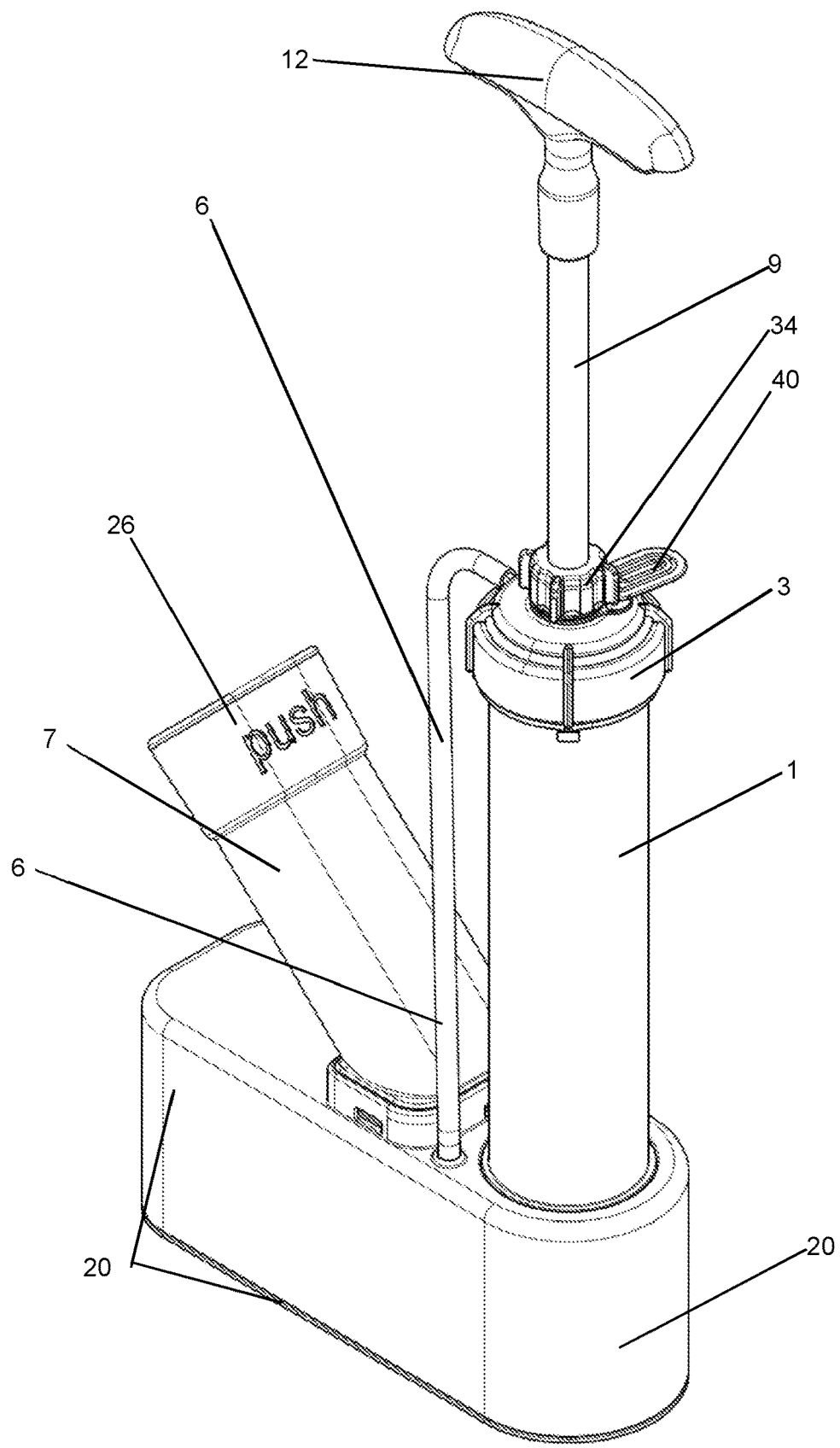
Figure 3:
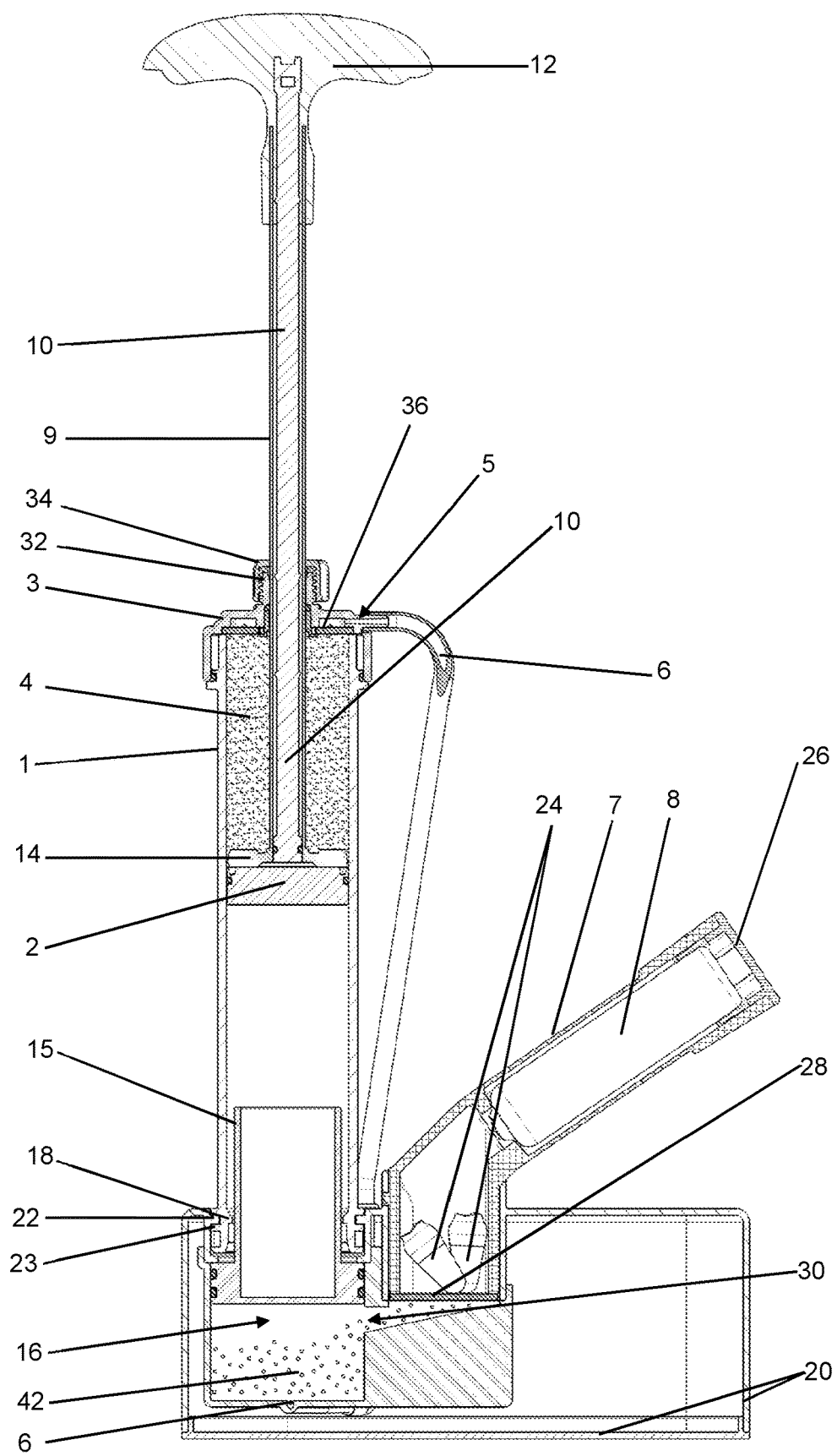
Figure 4:
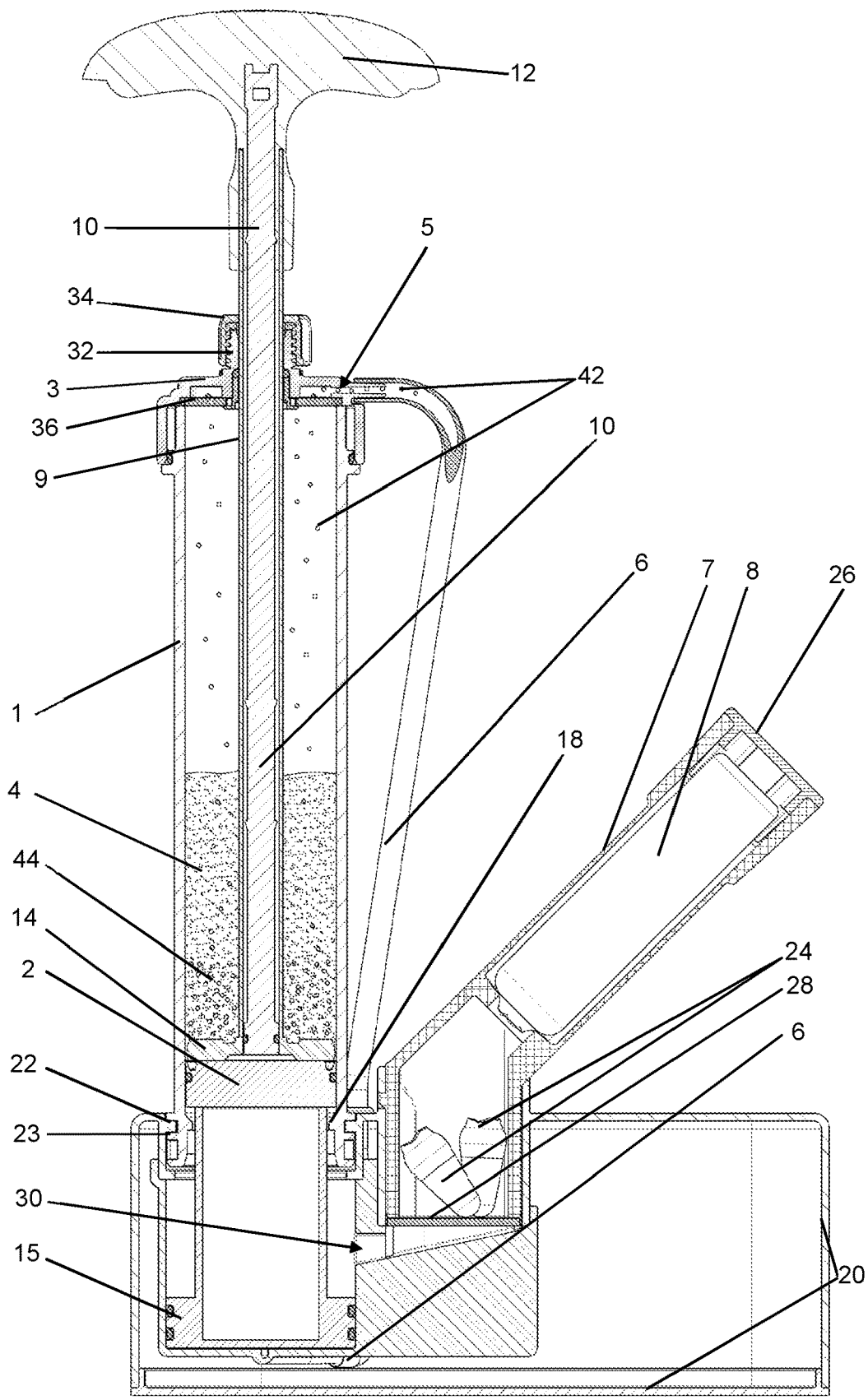
Figure 5:
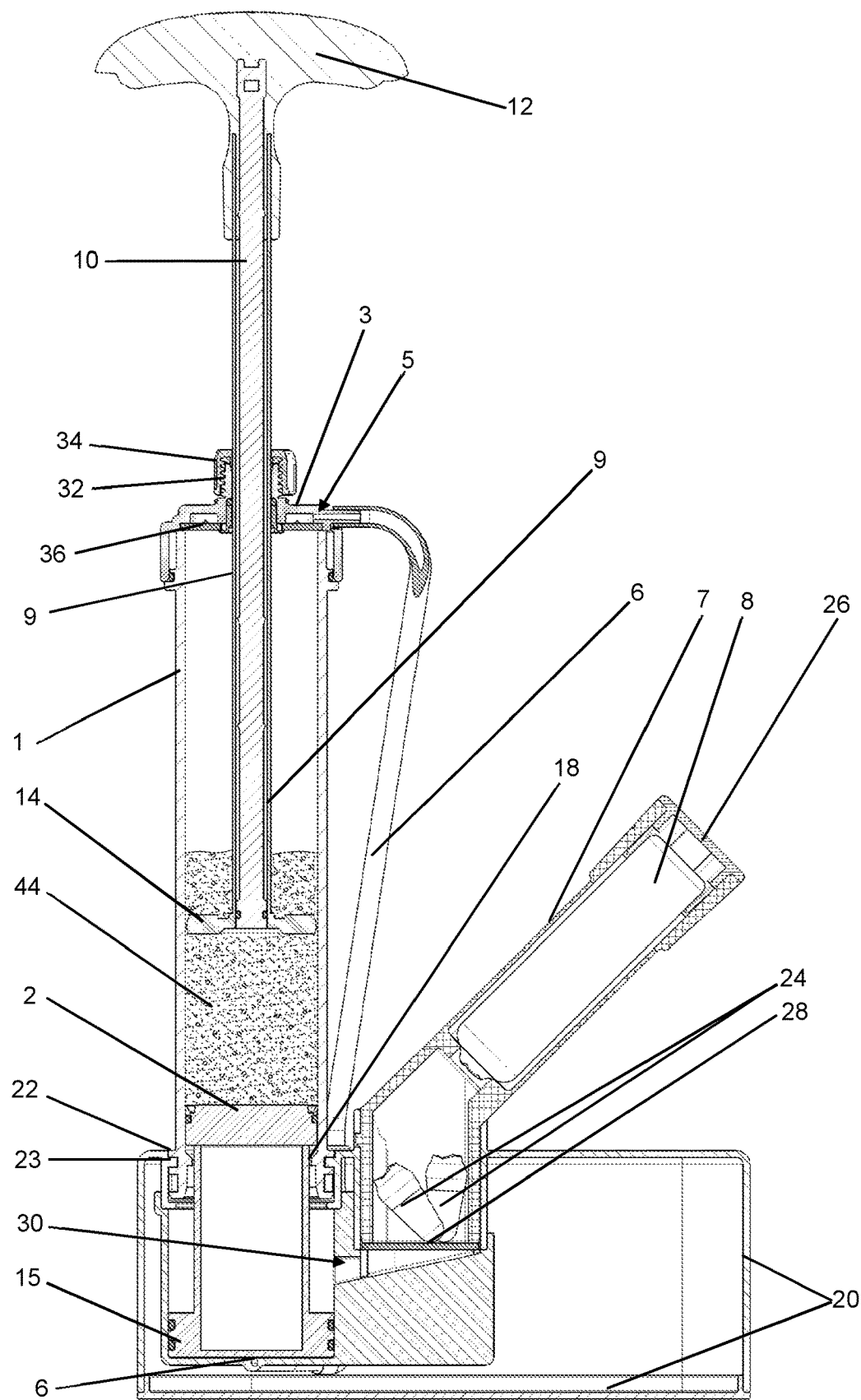
Figure 6:
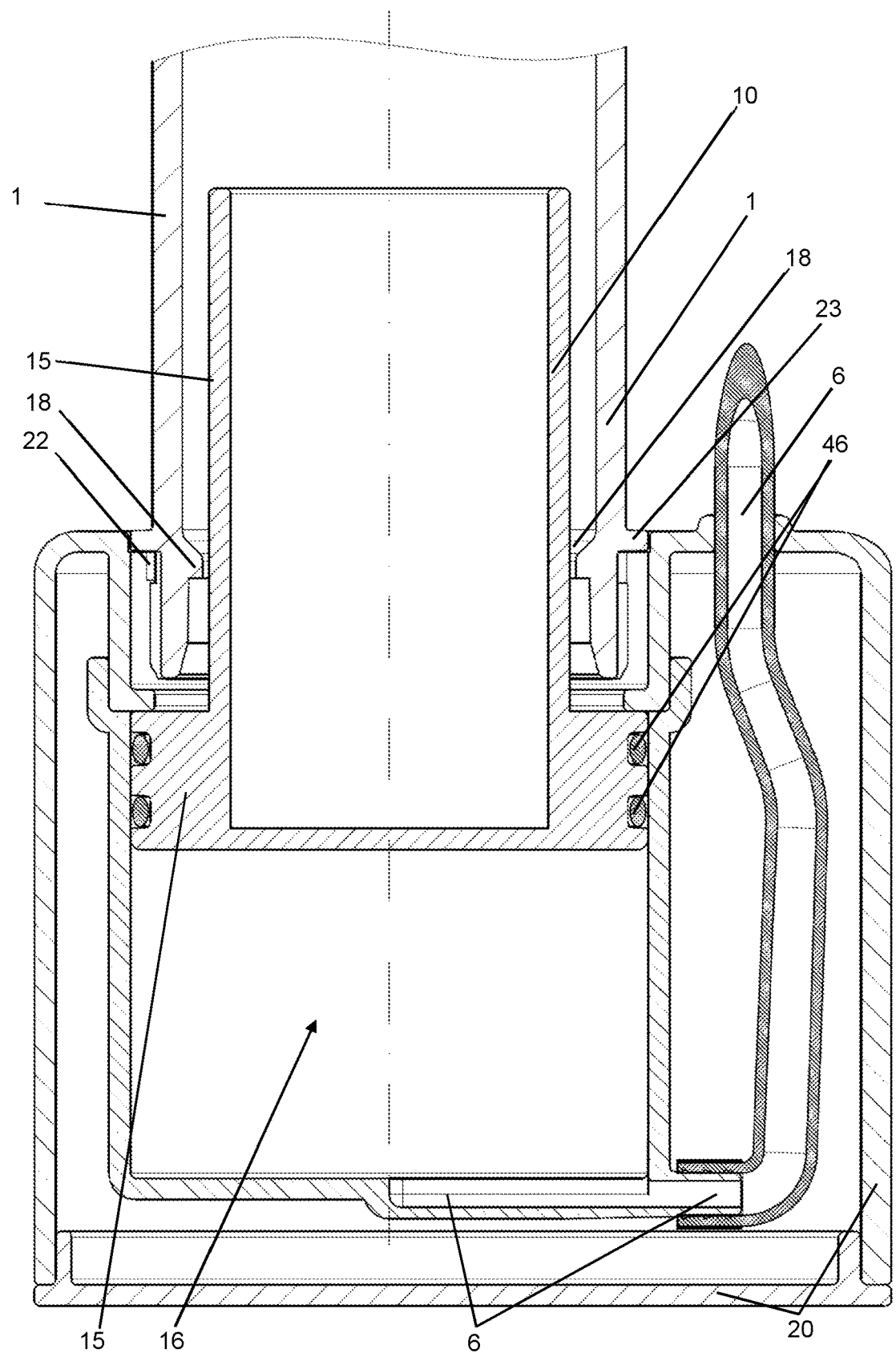
Figure 7:
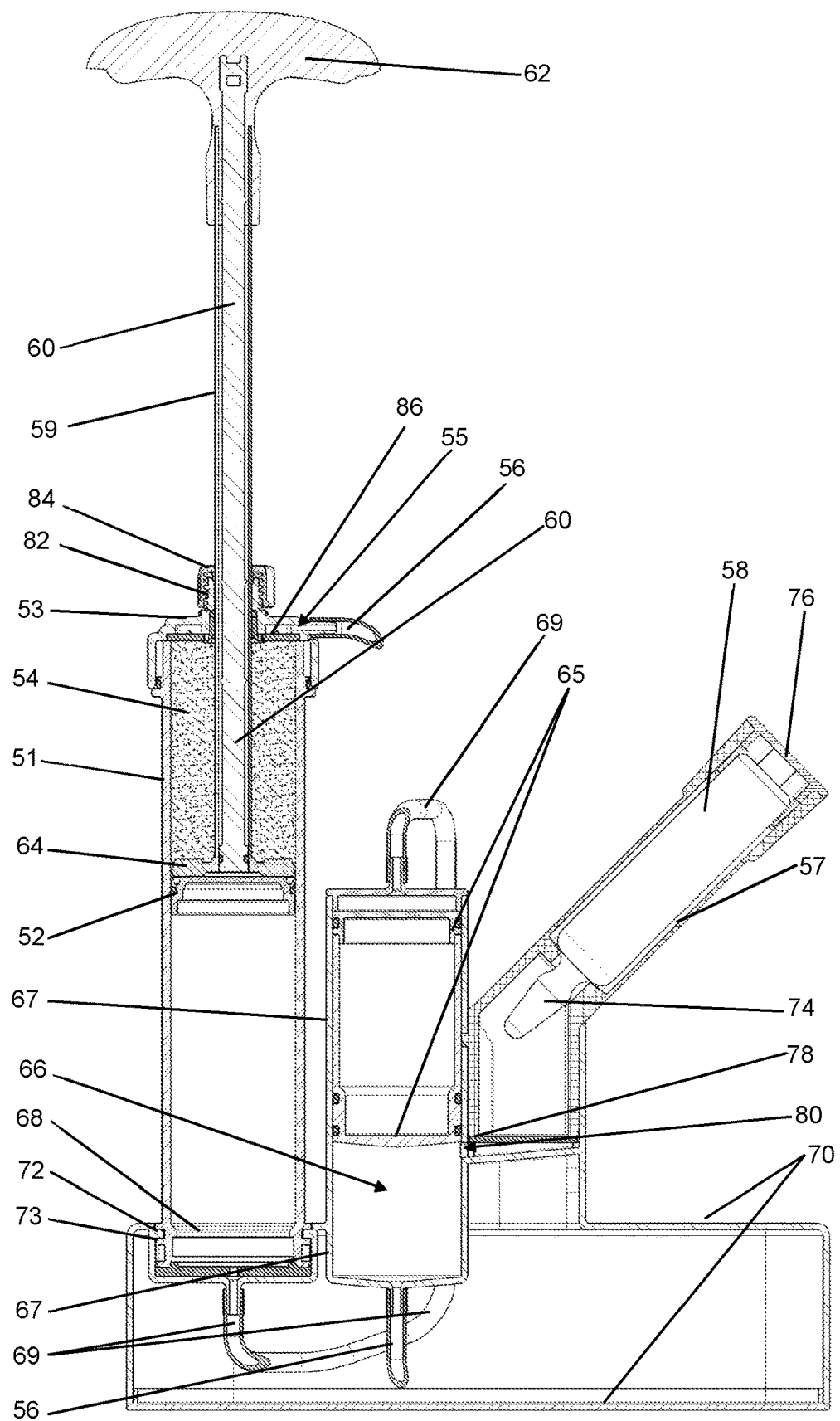
Figure 8:
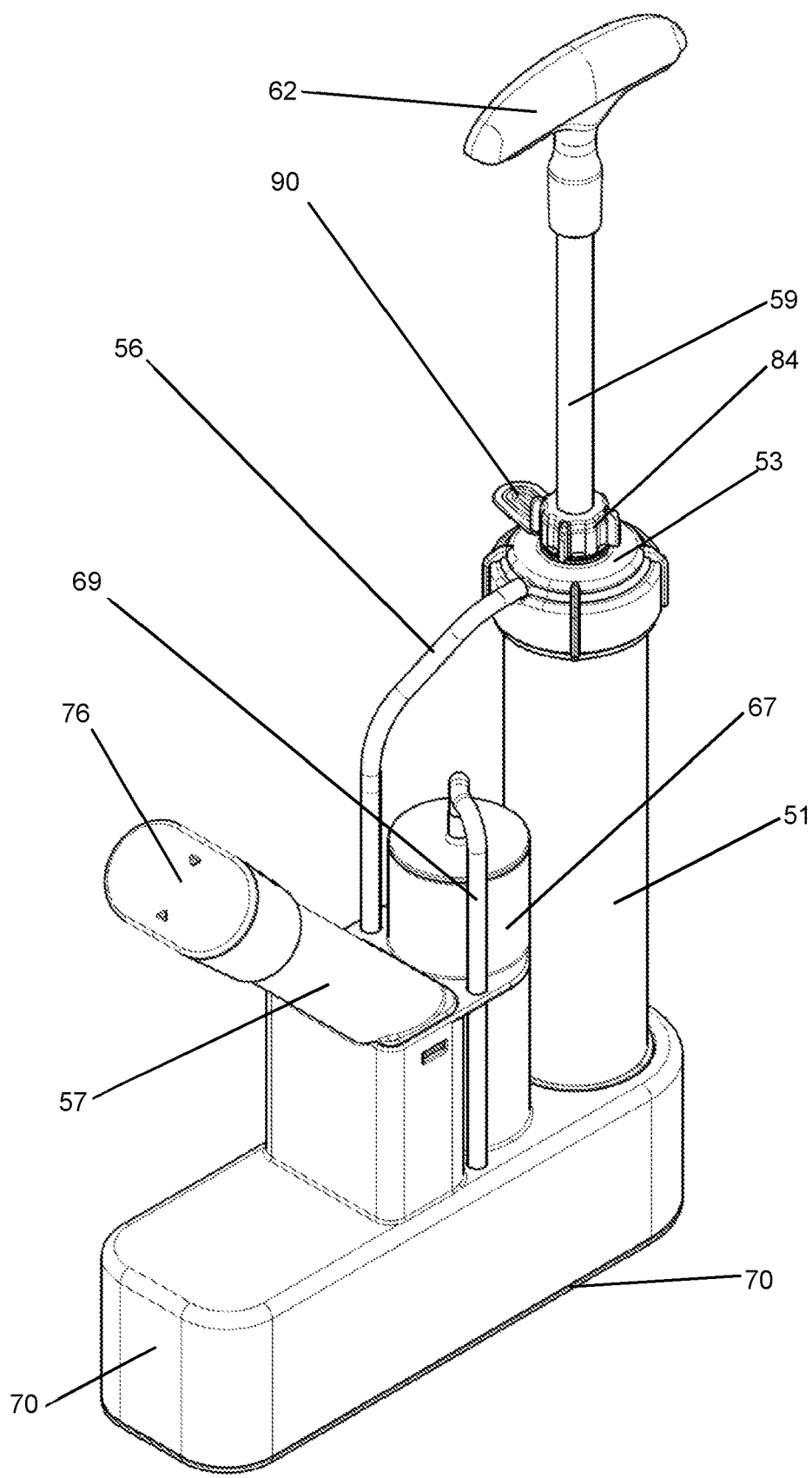
Figure 9:
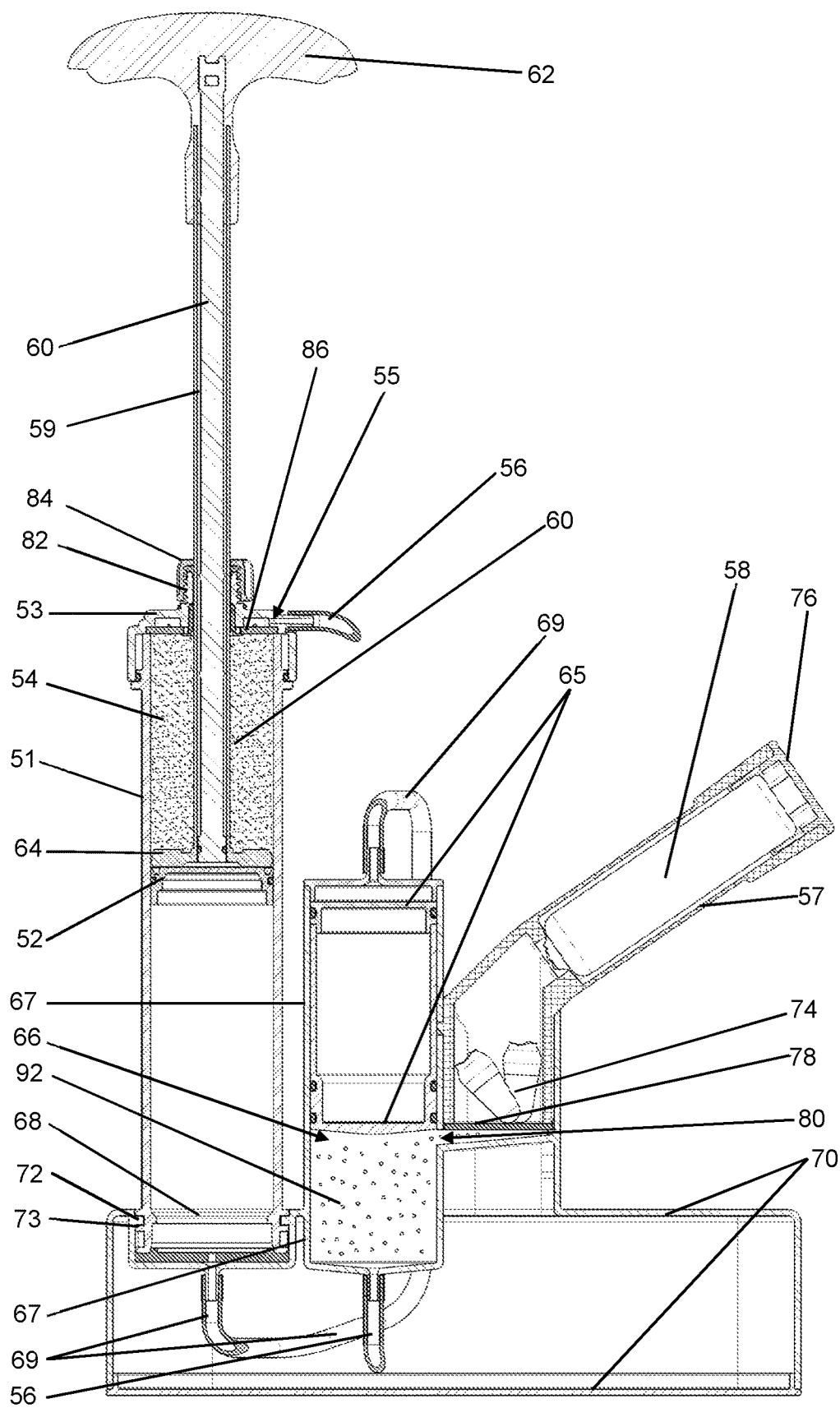
Figure 10:
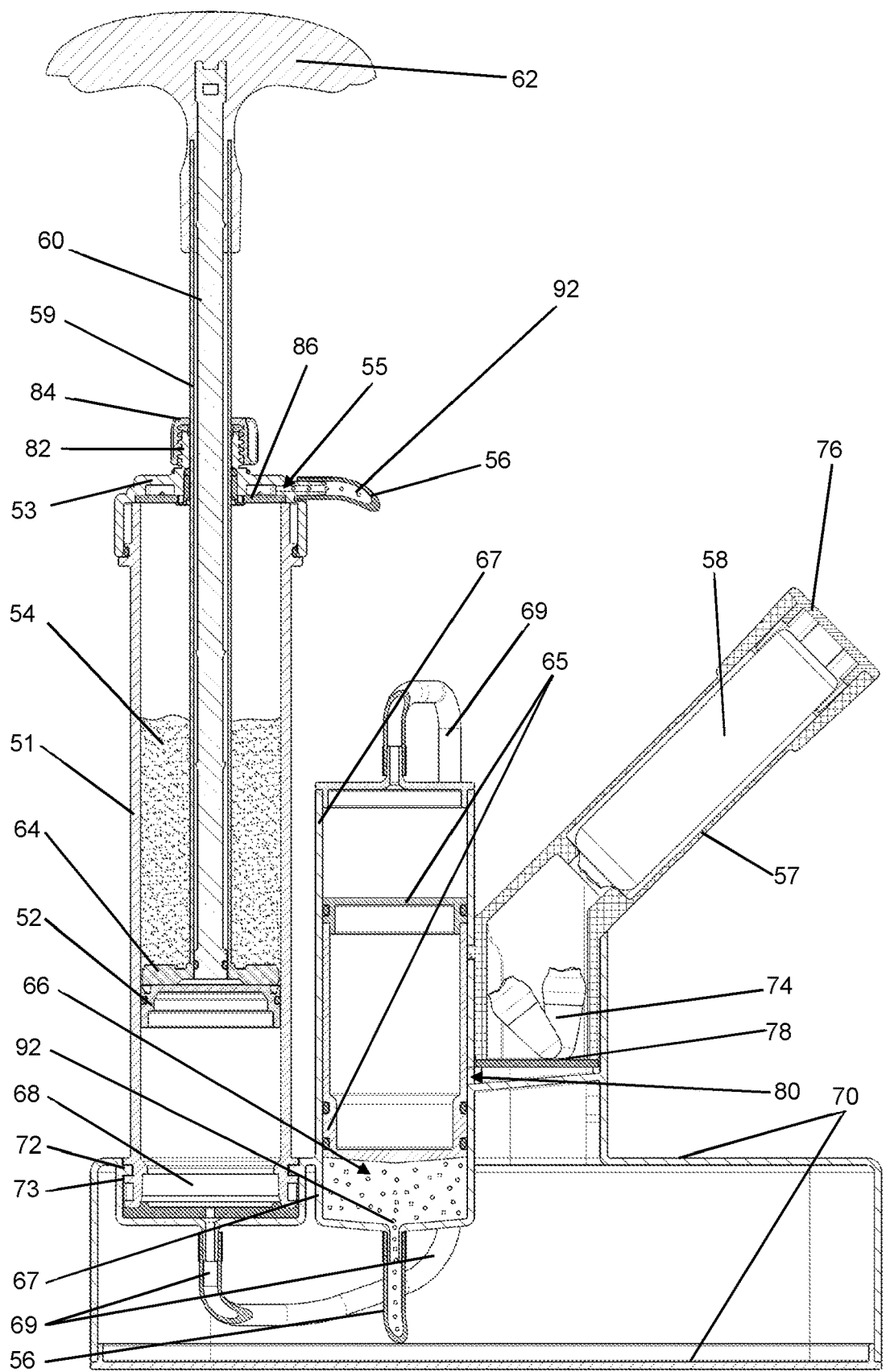
Figure 11:
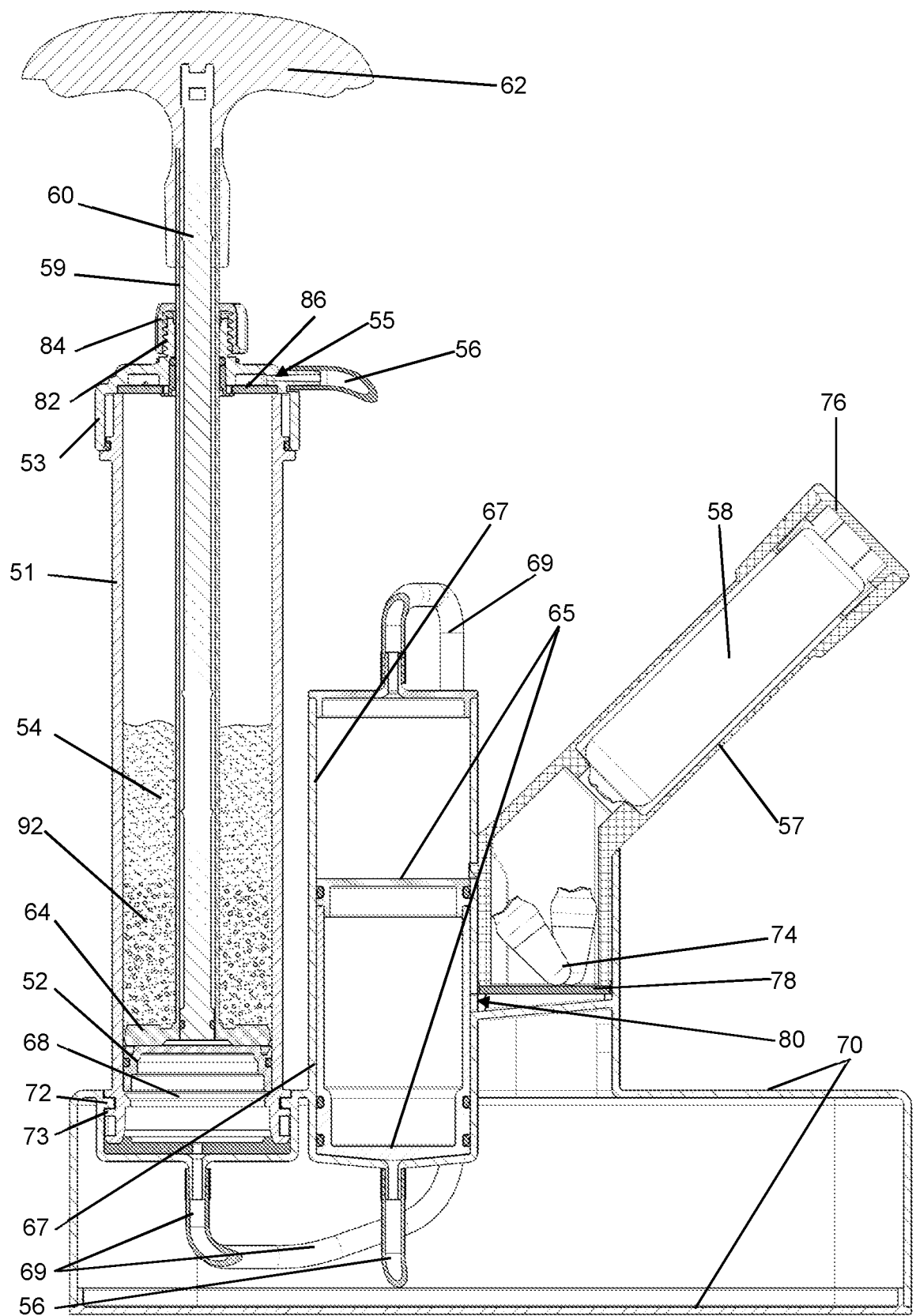
Figure 12:
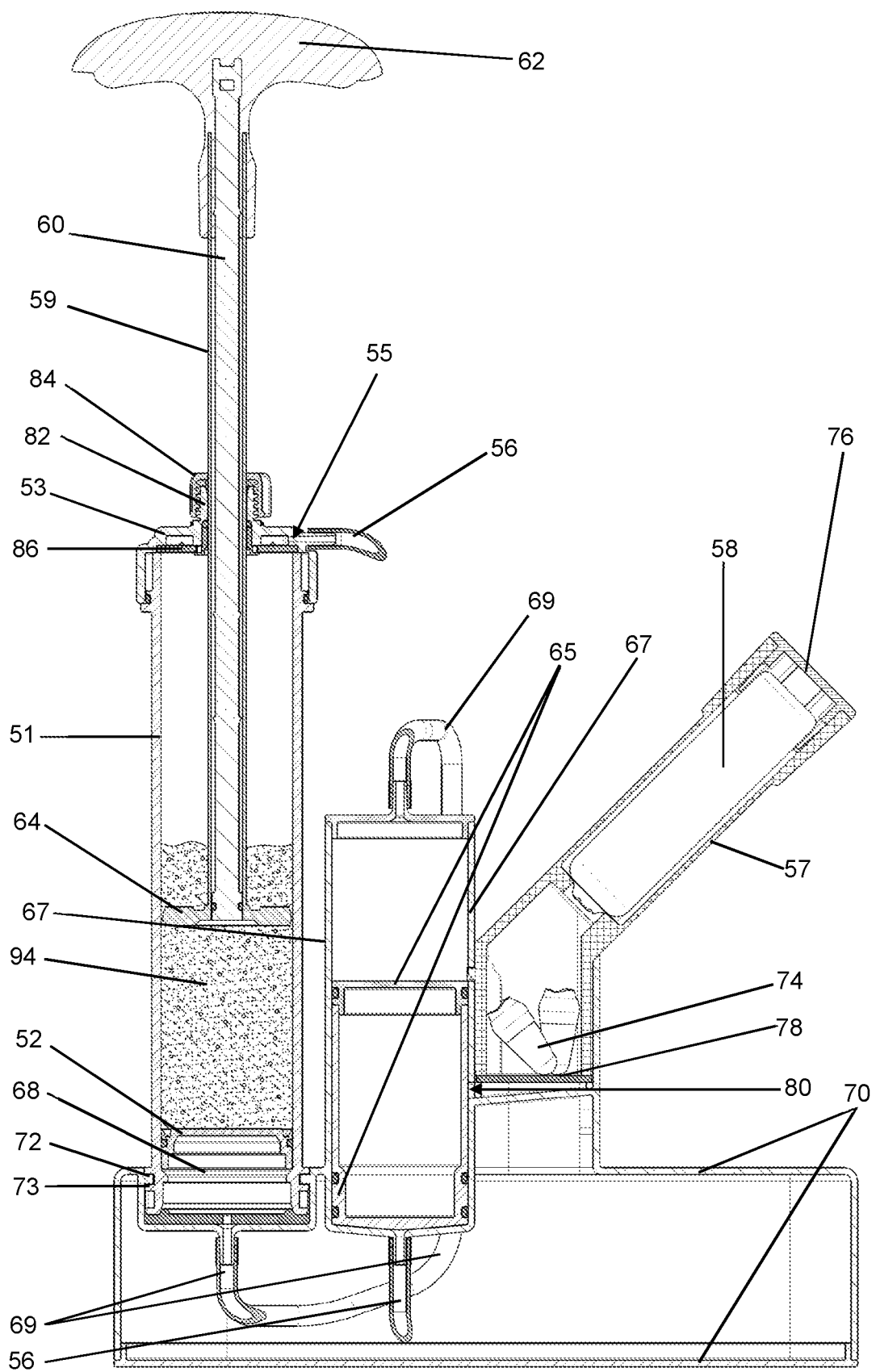
Figure 13:
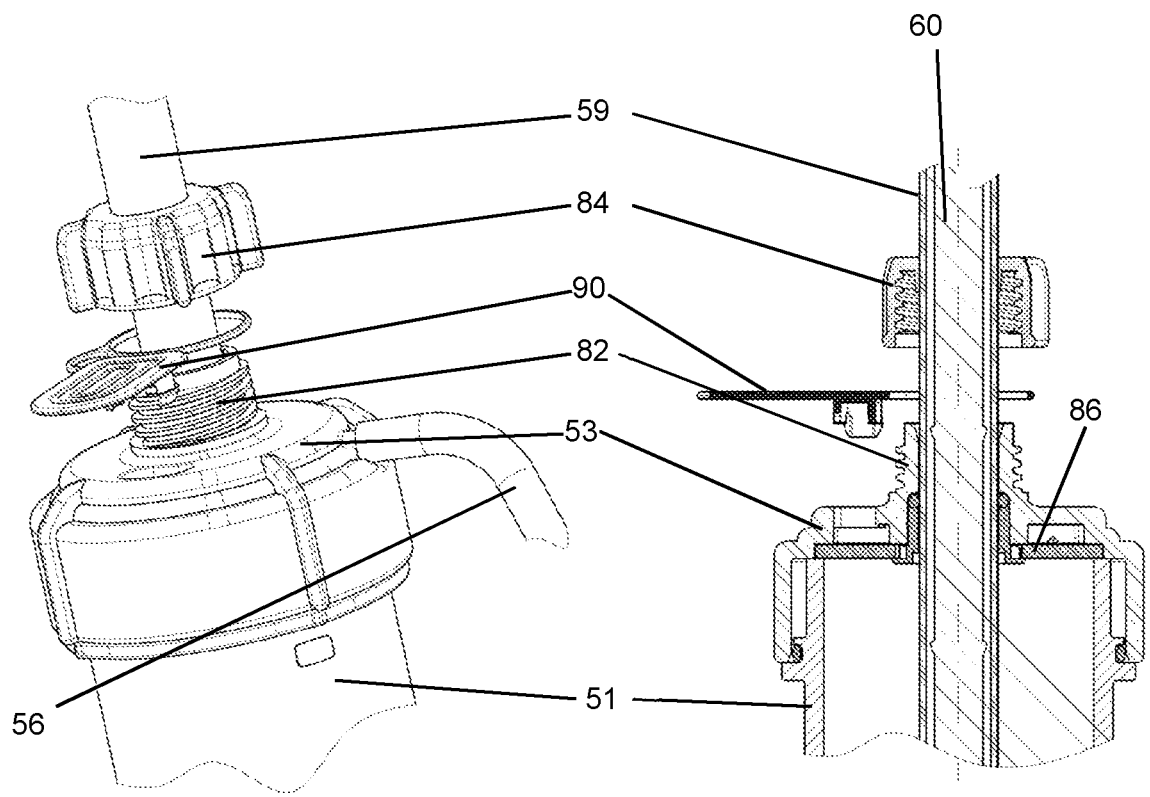

Further embodiments of the invention will be explained below with reference to thirteen schematic figures, without limiting the invention in any way however. The figures show:

FIG. 1: a schematic cross-sectional view of a first exemplary storage and mixing device according to the invention in the initial state;

FIG. 2: a schematic perspective view of the storage and mixing device according to FIG. 1;

FIG. 3: a schematic cross-sectional view of the first exemplary storage and mixing device where the monomer liquid container has been opened;

FIG. 4: a schematic cross-sectional view of the first exemplary storage and mixing device when or after the monomer liquid is or has been pressed in;

FIG. 5: a schematic partial cross-sectional view of the first exemplary storage and mixing device where the bone cement paste has been mixed;

FIG. 6: a schematic cross-sectional view of the lower part of the first exemplary storage and mixing device where the sectional plane is perpendicular to those in FIGS. 1, 3, 4 and 5;

FIG. 7: a schematic cross-sectional view of a second exemplary storage and mixing device according to the invention in the initial state;

FIG. 8: a schematic perspective view of the second exemplary storage and mixing device according to FIG. 7;

FIG. 9: a schematic cross-sectional view of the second exemplary storage and mixing device where the monomer liquid container has been opened;

FIG. 10: a schematic cross-sectional view of the second exemplary storage and mixing device when the monomer liquid is pressed in;

FIG. 11: a schematic cross-sectional view of the second exemplary storage and mixing device after the monomer liquid has been pressed in;

FIG. 12: a schematic partial cross-sectional view of the second exemplary storage and mixing device where the bone cement paste has been mixed; and FIG. 13: two enlarged sections of the upper region of the second storage and mixing device according to the invention, a schematic perspective view on the left and a schematic partial cross-sectional view on the right.

FIGS. 1 to 6 show an exemplary embodiment of a first storage and mixing device according to the invention. Here, FIG. 1 shows a schematic cross-sectional view of the first exemplary storage and mixing device according to the invention in the initial state. The storage and mixing device comprises a cartridge 1 with a cylindrical interior in which a plunger 2 is arranged to be linearly movable in the axial direction. On the front side of the cartridge 1 (FIGS. 1 and 3 to 5, at the top), the interior or the cartridge 1 is closed by a cartridge head 3 similar to a lid or a cap. The cartridge head 3 is sealed against the cartridge 1 by means of a circumferential seal. In the interior of the cartridge 1, a bone cement powder 4 as the first parent component 4 of a PMMA bone cement is located between the plunger 2 and the cartridge head 3.

The plunger 2 is in gas-tight contact with the inner wall of the interior of the cartridge 1 by means of a circumferential rubber seal. In this way, movement of the plunger 2 away from the cartridge head 3 can cause a reduced pressure to be produced in the interior of the cartridge 1, which is passed on to a fluid line 6 through a feed-through 5 in the cartridge head 3 or acts on the fluid line 6.

A container 7, which is separate from the cartridge 1, is arranged next to the cartridge 1. A glass ampoule 8 is inserted into the container 7 upside down. The glass ampoule 8 is not shown in section in the sectional views of FIGS. 1 and 3 to 5, and is filled with a monomer liquid 42 (see FIGS. 3 and 4) in FIG. 1.

A central delivery opening is located in the cartridge head 3, with a hollow or tubular mixing rod 9 passing therethrough. The hollow mixing rod 9 is closed inside by means of a core 10 which is pullable out of the mixing rod 9. In the region of the delivery opening, the mixing rod 9 is sealed against the cartridge head 3 by means of a circumferential seal, so that the reduced pressure in the interior of the cartridge 1 cannot (or at least not so quickly) draw air between the cartridge head 3 and the mixing rod 9 into the interior of the cartridge 1, even when the mixing rod 9 is rotated and moved in the longitudinal direction in the delivery opening.

A handle 12 is arranged on the front end of the mixing rod 9, by means of which the mixing rod 9 can be manually moved in the longitudinal direction relative to the cartridge 1 and can be axially rotated. In addition, the handle 12 can be used to pull the core 10 out of the mixing rod 9 after a latching mechanism (not shown) has been released or a resistance has been overcome.

A mixing device 14 with a number of mixing blades 14 is affixed to the mixing rod 9 in the interior of the cartridge 1 between the plunger 2 and the cartridge head 3, so that the mixing device 14 will rotate and move axially in the interior of the cartridge 1 when the mixing rod 9 is rotated and moved relative to the cartridge 1. In this way, the contents in the interior of the cartridge 1 can be mechanically mixed with the aid of the mixing device 14 by means of the mixing rod 9.

A pump plunger 15 is inserted into the back side of the cartridge 1 and has a cylindrical attachment as an extension on its front side, which projects into the interior of the cartridge 1, below the plunger 2, but is spaced from the plunger 2 in its initial position (see FIG. 1). The pump plunger 15 is supported to be movable in the longitudinal direction in a cylindrical receptacle 16 and sealed against the inner wall of the cylindrical receptacle 16 by means of two circumferential seals 46 (see FIG. 6). For this purpose, the receptacle 16 is arranged adjoining and below the cartridge 1. The fluid line 6 leads into the receptacle 16 on the lower side of the receptacle 16.

The fluid line 6 extends downwards, parallel to the axis of the cylindrical cartridge 1, away from the cartridge head 3, in some regions, then makes a curve and continues upwards to the mouth leading into the receptacle 16. The receptacle 16 could also be regarded as a widening of the fluid line 6. The receptacle 16 forms a reservoir for the monomer liquid 42 from the glass ampoule 8.

To produce a reduced pressure in the interior of the cartridge 1, the plunger 2 can be moved in the direction of a back side of the cartridge 1 (at the bottom, i.e. downwards in FIGS. 1 to 6) or in the direction of the back side of the interior of the cartridge 1, by manually pushing the plunger 2 in the direction of the back side with the aid of the mixing rod 9. To prevent the plunger 2 from being able to be pushed out of the interior of the cartridge 1 at the bottom, a stop 18 in the form of a circumferential bead is provided on the inner side of the cartridge 1 in the region of the back side of the interior. The plunger 2 can therefore only be pushed as far as the stop 18 in the direction of the back side of the cartridge 1. However, its movement is already blocked earlier by the pump plunger 15 when it has reached the base of the receptacle 16. After the cartridge 1 has been removed from the storage and mixing device, however, the stop 18 ensures that the plunger 2 cannot exit via the back side of the cartridge 1.

This is because the cartridge 1 is releasably connected to a foot part 20. Two circumferential projections 22 are arranged on the outside of the back side of the cartridge 1 in order to affix it to the foot part 20. For this purpose, the cartridge 1 is engaged with the foot part 20 by means of a holder 23 at the bottom, i.e. in the region of the back side. The aforesaid projections 22 can also be used to affix a press-out device (not shown) by means of which the ready-mixed bone cement paste 44 (see FIG. 5) can be applied. For this purpose, the plunger 2 is pushed into the cartridge 1 in the direction of the cartridge head 3 as a delivery plunger 2, by means of the press-out device actuated via an advanceable rod, thus pressing out the bone cement paste 44 through the delivery pipe 9 or the hollow mixing rod 9.

The glass ampoule 8 has a breakable ampoule head 24. When the ampoule head 24 is broken off or broken open, the glass ampoule 8 will be opened. The container 7 is made of an elastically deformable material which has a thickening on the neck between the ampoule head 24 and the body of the ampoule 8. In this way, the ampoule head 24 is securely supported, while the body of the ampoule 8 can be moved due to the elasticity of the insert that forms the container 7. The glass ampoule 8 can therefore be broken open within the storage and mixing device. On the back side of the container 7, a plug 26 is provided as a lid 26 by means of which the glass ampoule 8 is held in position. The lid 26 is provided with two openings through which air can flow into the interior of the container 7.

A filter 28 and/or screen 28 is arranged in the connection between the container 7 and the receptacle 16 or below the container 7, which keeps back fragments or glass splinters of the glass ampoule 8 which may be produced when the glass ampoule 8 is broken open. Below the filter 28 and/or screen 28, the base is inclined and the container 7 and the receptacle 16 are connected to each other in a liquid-permeable manner by an opening 30. After the glass ampoule 8 has been opened, the monomer liquid 42 flows downwards, across an inclined surface and through the opening 30, into the receptacle 16 (see FIG. 3). Here, the broken ampoule head 24 and any glass splinters produced are retained by the screen 28 and/or the filter 28.

A fitting 32 with an outer thread is provided on the cartridge head 3 in the region of the delivery opening. A conical sleeve nut 34 can be screwed onto this outer thread as a fastening device 34 in order to fix the mixing rod 9 relative to the cartridge head 3. To be able to fix the mixing rod 9 relative to the cartridge head 3, the sleeve nut 34 is screwed further onto the outer thread of the fitting 32. To prevent this at first or to avoid inadvertent fixation, an extractable securing device (not shown) in the form of a buckle with a gripping tab can be provided, which is arranged between the sleeve nut 34 and the cartridge head 3.

When the securing device is pulled off, the sleeve nut 34 can be screwed further onto the outer thread of the fitting 32, so that the fitting 32 is compressed, thus fixing the mixing rod 9 relative to the cartridge head 3.

An additional lateral opening is provided in the cartridge head 3, through which the interior of the cartridge 1 is accessible by sterilizing gases, such as ethylene oxide. As shown, the lateral opening is closed by means of a closure 40.

A porous disc 36 or a porous filter 36 is arranged between the cartridge head 3 and the interior of the cartridge 1, which disc or filter is permeable to gases and liquids but impermeable to powders and solid materials, such as the bone cement powder 4, so that the feed-through 5 is connected to the remaining interior of the cartridge 1 only via the porous filter 36. The porous filter 36 prevents the bone cement powder 4 from making its way into the fluid line 6, and therefore an inadvertent premature reaction of the bone cement powder 4 with the monomer liquid 42 and hence an inadvertent blocking of the thin part of the fluid line 6.

FIGS. 1 to 6 are used below to describe an exemplary method according to the invention, which is carried out using the storage and mixing device according to the invention. The fully assembled storage and mixing device is provided, as shown in FIGS. 1 and 2. The glass ampoule 8 is opened by breaking off the ampoule head 24, so that the monomer liquid 42 flows out of the glass ampoule 8, through the filter 28 and/or the screen 28 and the opening 30, into the receptacle 16 and into the lower region of the fluid line 6. Here, fragments of the glass and the broken ampoule head 24 are retained by the screen 28 and/or the filter 28. The monomer liquid 42 from the glass ampoule 8 has now been filled into the receptacle 16 and the fluid line 6 and is ready for use. This situation is shown in FIG. 3.

To produce a reduced pressure in the interior of the cartridge 1 in order to avoid gas inclusions in the bone cement paste 44 (see FIG. 6) and also to transfer the monomer liquid 42 into the interior of the cartridge 1, the plunger 2 is pushed in the direction of the back side of the cartridge 1 with the aid of the mixing rod 9. As a result, the volume between the plunger 2 and the cartridge head 3 in the interior of the cartridge 1 enlarges, so that a reduced pressure is produced. The air between the plunger 2 and the pump plunger 15 can escape to the outside, so that no overpressure builds up between the plunger 2 and the pump plunger 15. The plunger 2 meets the pump plunger 15 after it has covered the distance between the plunger 2 and the pump plunger 15 and pushes it towards the mouth of the fluid line 6 leading into the receptacle 16. Here, the opening 30 closes and the monomer liquid 42 is pressed out of the receptacle 16 into the fluid line 6 and later, through the fluid line 6 and the feed-through 5, into the interior of the cartridge 1 between the plunger 2 and the cartridge head 3. In addition, the reduced pressure sucks the monomer liquid 42 out of the fluid line 6 into the cartridge 1 and finally into the cartridge 1 (see FIG. 4) via the feed-through 5 and the porous filter 30. At the beginning (see FIG. 1), the plunger 2 is spaced from the back side or the stop 18 to an extent that the total stroke of the plunger 2 to reach the stop 18 is sufficient for the pressure in the interior of the cartridge 1 between the plunger 2 and the cartridge head 3 to reduce by at least half. The pump plunger 15 is pushed into the receptacle 16 as far as the stop in order to press all of the monomer liquid 42 out of the receptacle 16. A residual quantity of the monomer liquid 42 remains in the fluid line 6.

When the monomer liquid 42 has been pressed into the interior of the cartridge 1 by means of the pump plunger 15, it can be mixed with the bone cement powder 4 with the aid of the mixing device 14, by axially moving the mixing device 14 in the longitudinal direction and rotating it in the interior of the cartridge 1 manually with the aid of the mixing rod 9. In this way, the ready-mixed bone cement paste 44 (see FIG. 6) is produced. The mixing device 14 is then pulled towards the cartridge head 3 as far as the stop with the aid of the mixing rod 9, any securing device present (not shown) is removed and the mixing rod 9 is fixed relative to the cartridge head 3 by means of the sleeve nut 34. The core 10 is pulled out of the mixing rod 9 with the aid of the handle 12. The mixing rod 9 now forms a delivery pipe 9 which is arranged in the delivery opening or passes through the delivery opening and through which the ready-mixed bone cement paste 44 can be applied.

For this purpose, the cartridge 1 is separated from the foot part 20 by pulling it out and pulling the fluid line 6 off the feed-through 5. A one-way valve (not shown) can be provided in the fluid line 6 in order to prevent the residual monomer liquid 42 from exiting the fluid line 6. The cartridge 1 is then inserted into a press-out device (not shown), by means of which the plunger 2 can be pushed in the direction of the cartridge head 3 as a delivery plunger 2 with the aid of an advanceable rod. In this way, the bone cement paste 44 is pressed out through the delivery pipe 9 and through the delivery opening. No bone cement paste 44 can escape through the feed-through 5 as the porous filter 36 holds back the bone cement paste 44.

FIGS. 7 to 13 show an exemplary embodiment of an alternative second storage and mixing device according to the invention. Here, FIG. 7 shows a schematic cross-sectional view of the first exemplary storage and mixing device according to the invention in the initial state. The storage and mixing device comprises a cartridge 51 with a cylindrical interior in which a plunger 52 is arranged to be linearly movable in the axial direction. On the front side of the cartridge 51 (FIGS. 7 and 9 to 13, at the top), the interior or the cartridge 51 is closed by a cartridge head 53 similar to a lid or a cap. The cartridge head 53 is sealed against the cartridge 51 by means of a circumferential seal. In the interior of the cartridge 51, a bone cement powder 54 as the first parent component 54 of a PMMA bone cement is located between the plunger 52 and the cartridge head 53.

The plunger 52 is in gas-tight contact with the inner wall of the interior of the cartridge 51 by means of a circumferential rubber seal. In this way, movement of the plunger 52 away from the cartridge head 53 can cause a reduced pressure to be produced in the interior of the cartridge 51 between the plunger 52 and the cartridge head 53, which is passed on to a fluid line 56 through a feed-through 55 in the cartridge head 53 or acts on the fluid line 56, and cause an overpressure to be produced between the plunger 52 and a closure on the back side of the cartridge 51 or cause a pressure to be exerted on a hydraulic fluid contained therein (not shown).

A container 57, which is separate from the cartridge 51, is arranged next to the cartridge 51. A glass ampoule 58 is inserted into the container 57 upside down. The glass ampoule 58 is not shown in section in the sectional views of FIGS. 7 and 9 to 12, and is filled with a monomer liquid 92 (see FIGS. 9 to 11) in FIG. 7.

A central delivery opening is located in the cartridge head 53, with a hollow or tubular mixing rod 59 passing therethrough. The hollow mixing rod 59 is closed inside by means of a core 60 which is pullable out of the mixing rod 59. In the region of the delivery opening, the mixing rod 59 is sealed against the cartridge head 53 by means of a circumferential seal, so that the reduced pressure in the interior of the cartridge 51 cannot (or at least not so quickly) draw air between the cartridge head 53 and the mixing rod 59 into the interior of the cartridge 51, even when the mixing rod 59 is rotated and moved in the longitudinal direction in the delivery opening.

A handle 62 is arranged on the front end of the mixing rod 59, by means of which the mixing rod 59 can be manually moved in the longitudinal direction relative to the cartridge 51 and can be axially rotated. In addition, the handle 62 can be used to pull the core 60 out of the mixing rod 59 after a latching mechanism (not shown) has been released or a resistance has been overcome.

A mixing device 64 with a number of mixing blades 64 is affixed to the mixing rod 59 in the interior of the cartridge 51 between the plunger 52 and the cartridge head 53, so that the mixing device 64 will rotate and move axially in the interior of the cartridge 51 when the mixing rod 59 is rotated and moved relative to the cartridge 51. In this way, the contents in the interior of the cartridge 51 can be mechanically mixed with the aid of the mixing device 64 by means of the mixing rod 59.

A pump plunger 65 is arranged above a receptacle 66 in a hollow cylinder 67. The hollow cylinder 67 is arranged next to the cartridge 51 and delimits the receptacle 66 laterally and at the bottom, wherein the pump plunger 65 delimits the receptacle 66 at the top. To prevent the plunger 52 from being able to be pushed out of the interior of the cartridge 51 at the bottom, a stop 68 in the form of a circumferential bead is provided on the inner side of the cartridge 51 in the region of the back side of the interior. The plunger 52 can therefore only be pushed as far as the stop 68 in the direction of the back side of the cartridge 51. After the cartridge 51 has been removed from the storage and mixing device, the stop 68 ensures that the plunger 52 cannot exit via the back side of the cartridge 51.

The back side of the cartridge 51 is closed to be pressure-tight, and a gas line 69 or hydraulic line 69 is connected to the base of the closure and connects the back side of the cartridge 51 to the upper side of the hollow cylinder 67. The pump plunger 65 is in pressure-tight contact with the inner walls of the hollow cylinder 67 with the aid of three circumferential seals. The pump plunger 65 is supported to be movable in the longitudinal direction in the cylindrical cavity formed by the hollow cylinder 67. The fluid line 56 leads into the receptacle 66 on the lower side of the receptacle 66.

The fluid line 56 extends downwards, parallel to the axis of the cylindrical cartridge 51, away from the cartridge head 53, in some regions, then makes a curve and continues upwards to the mouth leading into the receptacle 66. The receptacle 66 could also be regarded as a widening of the fluid line 56. The receptacle 66 forms a reservoir for the monomer liquid 92 from the glass ampoule 58.

To produce a reduced pressure in the interior of the cartridge 51, the plunger 52 can be moved in the direction of a back side of the cartridge 51 (at the bottom, i.e. downwards in FIGS. 7 to 12) or in the direction of the back side of the interior of the cartridge 51, by manually pushing the plunger 52 in the direction of the back side with the aid of the mixing rod 59.

The cartridge 51 is releasably connected to a foot part 70. Two circumferential projections 72 are arranged on the outside of the back side of the cartridge 51 in order to affix it to the foot part 70. For this purpose, the cartridge 51 is engaged with the foot part 70 by means of a holder 73 at the bottom, i.e. in the region of the back side. The aforesaid projections 72 can also be used to affix a press-out device (not shown) by means of which the ready-mixed bone cement paste 94 (see FIG. 12) can be applied. For this purpose, the plunger 52 is pushed into the cartridge 51 in the direction of the cartridge head 53 as a delivery plunger 52, by means of the press-out device actuated via an advanceable rod, thus pressing out the bone cement paste 94 through the delivery pipe 59 or the hollow mixing rod 59.

The glass ampoule 58 has a breakable ampoule head 74. When the ampoule head 74 is broken off of broken open, the glass ampoule 58 will be opened. The container 57 is made of an elastically deformable material which has a thickening on the neck between the ampoule head 74 and the body of the ampoule 58. In this way, the ampoule head 74 is securely supported, while the body of the ampoule 58 can be moved due to the elasticity of the insert that forms the container 57. The glass ampoule 58 can therefore be broken open within the storage and mixing device. On the back side of the container 57, a plug 76 is provided as a lid 76 by means of which the glass ampoule 58 is held in position. The lid 76 is provided with two openings (see FIG. 8) through which air can flow into the interior of the container 57.

A filter 78 and/or screen 78 is arranged in the connection between the container 57 and the receptacle 66 or below the container 57, which keeps back fragments or glass splinters of the glass ampoule 58 which may be produced when the glass ampoule 58 is broken open. Below the filter 78 and/or screen 78, the base is inclined and the container 57 and the receptacle 66 are connected to each other in a liquid-permeable manner by an opening 80. After the glass ampoule 58 has been opened, the monomer liquid 92 flows downwards, across an inclined surface and through the opening 80, into the receptacle 66 (see FIG. 9). Here, the broken ampoule head 74 and any glass splinters produced are retained by the screen 78 and/or the filter 78.

A fitting 82 with an outer thread is provided on the cartridge head 53 in the region of the delivery opening. A conical sleeve nut 84 can be screwed onto this outer thread as a fastening device 84 in order to fix the mixing rod 59 relative to the cartridge head 53. To be able to fix the mixing rod 59 relative to the cartridge head 53, the sleeve nut 84 is screwed further onto the outer thread of the fitting 82. To prevent this at first or to avoid inadvertent fixation, an extractable securing device (not shown) in the form of a buckle with a gripping tab can be provided, which is arranged between the sleeve nut 84 and the cartridge head 53. When the securing device is pulled off, the sleeve nut 84 can be screwed further onto the outer thread of the fitting 82, so that the fitting 82 is compressed, thus fixing the mixing rod 59 relative to the cartridge head 53.

An additional lateral opening is provided in the cartridge head 53, through which the interior of the cartridge 51 is accessible by sterilizing gases, such as ethylene oxide. As shown, the lateral opening is closed by means of a closure 90. The closure 90 is shown in the opened position in FIG. 13. In the opened position according to FIG. 13, the interior of the cartridge 51 can be sterilized through the opening arranged laterally next to the delivery opening in the cartridge head 53, by introducing a sterilizing gas, such as ethylene oxide. Then, the closure 40 can be pushed into the opening in order to close it. The sleeve nut 84 is then screwed onto the fitting 82 to such an extent that the mixing rod 59 is sealed against the cartridge head 53 but is still freely movable in the delivery opening.

A porous disc 86 or a porous filter 86 is arranged between the cartridge head 53 and the interior of the cartridge 51, which disc or filter is permeable to gases and liquids but impermeable to powders and solid materials, such as the bone cement powder 54, so that the feed-through 55 is connected to the remaining interior of the cartridge 51 only via the porous filter 86. The porous filter 86 prevents the bone cement powder 54 from making its way into the fluid line 56, and therefore an inadvertent premature reaction of the bone cement powder 54 with the monomer liquid 92 and hence an inadvertent blocking of the thin part of the fluid line 56.

FIGS. 7 to 12 are used below to describe an exemplary method according to the invention, which is carried out using the storage and mixing device according to the invention. The fully assembled storage and mixing device is provided, as shown in FIGS. 7 and 8. The glass ampoule 58 is opened by breaking off the ampoule head 74, so that the monomer liquid 92 flows out of the glass ampoule 58, through the filter 78 and/or the screen 78 and the opening 80, into the receptacle 66 and into the lower region of the fluid line 56. Here, fragments of the glass and the broken ampoule head 74 are retained by the screen 78 and/or the filter 78. The monomer liquid 92 from the glass ampoule 58 has now been filled into the receptacle 66 and the fluid line 56 and is ready for use. This situation is shown in FIG. 9.

To produce a reduced pressure in the interior of the cartridge 51 in order to avoid gas inclusions in the bone cement paste 94 (see FIG. 12) and also to transfer the monomer liquid 92 into the interior of the cartridge 51, the plunger 52 is pushed in the direction of the back side of the cartridge 51 with the aid of the mixing rod 59. As a result, the volume between the plunger 52 and the cartridge head 53 in the interior of the cartridge 51 enlarges, so that a reduced pressure is produced. At the same time, between the plunger 52 and the closed back side of the cartridge 51, an overpressure is produced, which is introduced into the hollow cylinder 67 at the top between the upper side of the hollow cylinder 67 and the pump plunger 65 through the gas line 69, or a hydrostatic pressure is produced, which is passed into the hollow cylinder 67 at the top between the upper side of the hollow cylinder 67 and the pump plunger 65 through the hydraulic line 69. The overpressure or the hydrostatic pressure causes the pump plunger 65 in the hollow cylinder 67 to be pushed downwards towards the mouth of the fluid line 56 leading into the receptacle 66. Here, the opening 80 closes and the monomer liquid 92 is pressed out of the receptacle 66 into the fluid line 56 and later, through the fluid line 56 and the feed-through 55, into the interior of the cartridge 51 between the plunger 52 and the cartridge head 53. In addition, the reduced pressure sucks the monomer liquid 92 out of the fluid line 56 into the cartridge 51 and finally into the cartridge 51 (see FIGS. 10 and 11) via the feed-through 55 and the porous filter 80. At the beginning of movement (see FIG. 7), the plunger 52 is spaced from the back side or the stop 68 to an extent that the total stroke of the plunger 52 to reach the stop 68 is sufficient for the pressure (gas pressure) in the interior of the cartridge 51 between the plunger 52 and the cartridge head 53 to reduce by at least half and for the overpressure which builds up between the plunger 52 and the closed back side of the cartridge 51 to be sufficient to exert pressure on the pump plunger 65 in the hollow cylinder 67 or the volume of the stroke to be equal to the volume of the stroke of the pump plunger 65.

As the space between the plunger 52 and the closed back side of the cartridge 51, in the gas line 69 or the hydraulic line 69 and between the pump plunger 65 and the upper side of the hollow cylinder 67, is closed, it can be provided that a hydraulic fluid (not shown) is provided in this closed space, by means of which the pressure can be transferred hydraulically through the hydraulic line 69.

The pump plunger 65 is pushed into the receptacle 66 as far as the stop in order to press all of the monomer liquid 92 out of the receptacle 66. A residual quantity of the monomer liquid 92 remains in the fluid line 56.

When the monomer liquid 92 has been pressed into the interior of the cartridge 51 by means of the pump plunger 65, it can be mixed with the bone cement powder 54 with the aid of the mixing device 64, by axially moving the mixing device 54 in the longitudinal direction and rotating it in the interior of the cartridge 51 manually with the aid of the mixing rod 59. In this way, the ready-mixed bone cement paste 94 (see FIG. 12) is produced. The mixing device 64 is then pulled towards the cartridge head 53 as far as the stop with the aid of the mixing rod 59, any securing device present (not shown) is removed and the mixing rod 59 is fixed relative to the cartridge head 53 by means of the sleeve nut 84. The core 60 is pulled out of the mixing rod 59 with the aid of the handle 62. The mixing rod 59 now forms a delivery pipe 59 which is arranged in the delivery opening or passes through the delivery opening and through which the ready-mixed bone cement paste 94 can be applied.

For this purpose, the cartridge 51 is separated from the foot part 70 by pulling it out and pulling the fluid line 56 off the feed-through 55. A one-way valve (not shown) can be provided in the fluid line in order to prevent the residual monomer liquid 92 from exiting the fluid line 56. The cartridge 51 is then inserted into a press-out device (not shown), by means of which the plunger 52 can be pushed in the direction of the cartridge head 53 as a delivery plunger 52 with the aid of an advanceable rod. In this way, the bone cement paste 94 is pressed out through the delivery pipe 59 and through the delivery opening. No bone cement paste 94 can escape through the feed-through 55 as the porous filter 86 holds back the bone cement paste 94.

The features of the invention disclosed in the above description, the claims, figures and exemplary embodiments can be relevant both individually and in combination for implementing the various embodiments of the invention.

LIST OF REFERENCE NUMERALS 1, 51 Cartridge
2, 52 Plunger/deliver plunger
3, 53 Cartridge head
4, 54 Bone cement powder/first parent component
5, 55 Feed-through
6, 56 Fluid line
7, 57 Container
8, 68 Monomer liquid container/glass ampoule
9, 59 Mixing rod/delivery pipe
10, 60 Core
12, 62 Handle
14, 64 Mixing blade/mixing device
15, 65 Pump plunger
16, 66 Receptacle
18, 68 Stop
20, 70 Foot part
22, 72 Projection
23, 73 Holder
24, 74 Ampoule head
26, 76 Lid/plug
28, 78 Screen/filter
30, 80 Opening
32, 82 Fitting with outer thread
34, 84 Conical sleeve nut/fastening device 36, 86 Porous filter/porous disc
40, 90 Closure
42, 92 Monomer liquid
44, 94 Mixed bone cement paste
46 Seal
67 Hollow cylinder
69 Gas line/hydraulic line

The invention claimed is:

1. A storage and mixing device for two-component polymethyl methacrylate bone cements, the storage and mixing device comprising:
- a cylindrical interior of a cartridge delimited on a front side by a cartridge head with a closed delivery opening;
- a plunger arranged to be axially movable in the cylindrical interior of the cartridge and spaced from the cartridge head, wherein the plunger circumferentially rests against the inner wall of the interior, so that the plunger divides the interior of the cartridge into two sections;
- a powdery first parent component of the bone cement contained in the interior between the plunger and the cartridge head;
- a feed-through arranged in the cartridge head or in a cylinder barrel of the cartridge between the plunger and the cartridge head, wherein the feed-through is connected to a fluid line;
- a receptacle for a monomer liquid, wherein the fluid line connects the feed-through to the receptacle in a liquid-permeable manner, wherein the monomer liquid as a second parent component of the bone cement is contained in the receptacle or is fillable or introducible into the receptacle; and
- a press-out device pushable into the receptacle, so that monomer liquid is pressable out of the receptacle into the fluid line, wherein
- the plunger is spaced from a back side of the cylindrical interior, located opposite the front side, so that, by moving the plunger in the direction of the back side, the press-out device is pushable into the receptacle and a reduced pressure is producible in the interior of the cartridge between the plunger and the cartridge head and
- a mouth for introducing the monomer liquid into the receptacle is arranged in the region of the press-out device, wherein the mouth is closed by pushing in the press-out device when the press-out device begins to move into the receptacle.

2. The storage and mixing device according to claim 1, wherein the plunger in the interior of the cartridge is pushable or pullable manually in the direction of the back side of the interior by means of a rod or another force transmission means, wherein an actuating means or a handle for operating the rod or the force transmission means is affixed to the rod or the force transmission means.

3. The storage and mixing device according to claim 1, further comprising:
- a porous filter arranged in the cartridge head, in the feed-through and/or in the fluid line, wherein the filter is permeable to the monomer liquid and impermeable to the powdery first parent component.

4. The storage and mixing device according to claim 1, wherein the plunger is spaced from a back side of the cylindrical interior, located opposite the front side, to an extent that the reduced pressure is able to suck the monomer liquid out of the fluid line into the interior of the cartridge.

5. The storage and mixing device according to claim 1, further comprises:
- a container separate from the cartridge and from the receptacle and in which the monomer liquid is contained, wherein the container is connected to the receptacle, via an opening, wherein a closed glass ampoule or a foil bag containing the monomer liquid is arranged or is arrangeable in the container, wherein the glass ampoule is breakable open within the container or the foil bag is pierceable open or tearable open within the container.

6. The storage and mixing device according to claim 5, wherein the cartridge, the receptacle, the separate container and the fluid line are connected to a common stand, wherein the receptacle, the container and the fluid line are permanently connected to the stand and the cartridge is releasably connected to the stand, the cartridge being screwed to the stand by means of a thread or connected to the stand by means of a latching mechanism.

7. The storage and mixing device according to claim 5, wherein the monomer liquid container, selected from the foil bag or the closed glass ampoule, is contained in the separate container, which is openable within the separate container, so that the monomer liquid flows out of the opened monomer liquid container into the receptacle, wherein an opening device for opening the monomer liquid container, operable from outside, is arranged on the container.

8. The storage and mixing device according to claim 1, further comprising:
- a mixing device arranged in the interior of the cartridge between the plunger and the cartridge head, by means of which the first parent component is mixable with the monomer liquid in the interior of the cartridge.

9. The storage and mixing device according to claim 8, wherein the mixing device is operable from outside the cartridge by means of a mixing rod, wherein the mixing rod passes through the cartridge head in a gas-tight manner and is rotatable and movable in the axial direction, the mixing rod passing through the delivery opening.

10. The storage and mixing device according to claim 9, wherein the plunger is pushable in the direction of the back side of the interior of the cartridge by means of the mixing rod.

11. The storage and mixing device according to claim 9, wherein the mixing rod is a delivery pipe in which a manually removable core is arranged, so that the mixed bone cement paste is dischargeable from the interior of the cartridge through the delivery pipe without the core.

12. The storage and mixing device according to claim 1, wherein, inside the interior of the cartridge on the back side, a stop is provided which limits the movement of the plunger in the direction of the back side.

13. The storage and mixing device according to claim 1, wherein the plunger has at least one latching element which is releasably engageable with a complementary latching element on the inner side of the cartridge in the region of the back side of the interior.

14. The storage and mixing device according to claim 1, wherein a closable gas-permeable opening is arranged in the cartridge head, wherein a porous disc which is permeable to gases and impermeable to solid particles is arranged between the first parent component and the opening, wherein the porous disc is arranged in the cartridge head.

15. The storage and mixing device according to claim 1, wherein the receptacle is arranged on the back side of the cartridge and the plunger pushes the press-out device into the receptacle during movement in the direction of the back side of the cartridge, wherein the region between the press-out device and the plunger is opened towards the outside.

16. The storage and mixing device according to claim 15, wherein the plunger is spaced from the press-out device, so that a reduced pressure is first built up in the interior of the cartridge, without the press-out device being moved, when the plunger is moved in the direction of the back side of the cartridge in a first section, and, in addition, the press-out device is pushed into the receptacle when the plunger is moved in a second section.

17. The storage and mixing device according to claim 15, wherein the press-out device is a pump plunger and the receptacle is a hollow cylinder in which the pump plunger is axially movable, wherein an extension, in the form of a cylindrical body, is arranged on the upper side of the pump plunger, which extension has an outer diameter smaller than or equal to the inner diameter of the interior of the cartridge, wherein the pump plunger with the extension is arranged in the hollow cylinder in such a manner that the extension projects into the interior of the cartridge.

18. The storage and mixing device according to claim 1, wherein the receptacle is delimited by a closed hollow cylinder separated from the cartridge and in which a pump plunger as a press-out device is supported to be axially movable, wherein the pump plunger is in circumferential and tight contact with the inner wall of the hollow cylinder, wherein the hollow cylinder is connected to the fluid line at a first lower, base and connected to the interior of the cartridge via a compressed gas line or a hydraulic line on the back side of the cartridge at a second, preferably upper, base, wherein the back side of the cartridge is closed except for the mouth leading into the compressed gas line or the hydraulic line, so that, during movement of the plunger in the direction of the back side of the interior, an overpressure or a pressure is produced in the space between the plunger and the back side, which is passed into the hollow cylinder through the compressed gas line or the hydraulic line.

19. A method for mixing the parent components of a bone cement using a storage and mixing device, wherein the method comprises:
  a) providing the storage and mixing device that comprises:
    a cylindrical interior of a cartridge delimited on a front side by a cartridge head with a closed delivery opening;
    a plunger arranged to be axially movable in the cylindrical interior of the cartridge and spaced from the cartridge head, wherein the plunger circumferentially rests against the inner wall of the interior, so that the plunger divides the interior of the cartridge into two sections;
    a powdery first parent component of the bone cement contained in the interior between the plunger and the cartridge head;
    a feed-through arranged in the cartridge head or in a cylinder barrel of the cartridge between the plunger and the cartridge head, wherein the feed-through is connected to a fluid line;
    a receptacle for a monomer liquid, wherein the fluid line connects the feed-through to the receptacle in a liquid-permeable manner, wherein the monomer liquid as a second parent component of the bone cement is contained in the receptacle or is fillable or introducible into the receptacle; and
    a press-out device pushable into the receptacle, so that monomer liquid is pressable out of the receptacle into the fluid line,
    wherein the plunger is spaced from a back side of the cylindrical interior, located opposite the front side, so that, by moving the plunger in the direction of the back side, the press-out device is pushable into the receptacle and a reduced pressure is producible in the interior of the cartridge between the plunger and the cartridge head;
  b) moving the plunger in the direction of the back side of the cylindrical interior of the cartridge, wherein a reduced pressure is produced in the interior of the cartridge between the plunger and the cartridge head due to said movement of the plunger;
  c) pushing the press-out device into the receptacle due to said movement of the plunger, whereby a monomer liquid contained in the receptacle is pressed into the interior of the cartridge through the fluid line due to said movement of the press-out device;
  d) mixing the monomer liquid and the first parent component to form the bone cement paste in the interior of the cartridge; and
  e) discharging the bone cement paste from the interior of the cartridge by advancing the plunger in the direction of the cartridge head.

20. The method according to claim 19, further comprising:
  sucking the monomer liquid out of the fluid line into the interior of the cartridge by the reduced pressure in the interior of the cartridge.

21. The method according to claim 19, further comprising:
  introducing the monomer liquid into the receptacle before a) after a monomer liquid container has been opened in a container of the storage and mixing device.

22. The method according to claim 19, wherein, in a), the plunger is pushed in the direction of the back side of the cartridge by means of a mixing rod, wherein the mixing rod is movably supported in the delivery opening in the cartridge head, and, in c), the monomer liquid is mixed with the first parent component by moving a mixing device, which is connected to the mixing rod, in the interior of the cartridge between the plunger and the cartridge head, by moving the mixing rod and therefore the mixing device.

23. The method according to claim 22, wherein the mixing device is pulled towards the cartridge head by means of the mixing rod and a core is removed from the mixing rod between c) and d), so that the mixing rod without the core forms a delivery pipe through which the mixed bone cement paste is pressed out of the interior of the cartridge in d).

24. The method according to claim 19, wherein before d), the cartridge is separated from the storage and mixing device and inserted into a press-out device by means of which the plunger is pushed in the direction of the cartridge head in d), using a tappet or an advanceable rod, in order to discharge the bone cement paste from the interior of the cartridge.

25. The method according to claim 19, wherein the receptacle is a hollow cylinder and the press-out device is a pump plunger which is arranged to be movable in the longitudinal direction in the hollow cylinder, wherein the pump plunger is moved in the hollow cylinder by exerting pressure with the plunger or is moved pneumatically or hydraulically by means of an overpressure or pressure produced in the interior between the back side of the cartridge and the plunger, wherein the overpressure is passed into the hollow cylinder through a compressed gas line or the pressure is passed into the hollow cylinder through a hydraulic line.

26. The method according to claim 19, wherein the glass ampoule or the foil bag is opened in the storage and mixing device before a) and b), wherein the monomer liquid flows out of the monomer liquid container and flows into the receptacle through a screen and/or a filter.

27. A storage and mixing device for two-component polymethyl methacrylate bone cements, the storage and mixing device comprising:
a cylindrical interior of a cartridge delimited on a front side by a cartridge head with a closed delivery opening;
a plunger arranged to be axially movable in the cylindrical interior of the cartridge and spaced from the cartridge head, wherein the plunger circumferentially rests against the inner wall of the interior, so that the plunger divides the interior of the cartridge into two sections;
a powdery first parent component of the bone cement contained in the interior between the plunger and the cartridge head;
a feed-through arranged in the cartridge head or in a cylinder barrel of the cartridge between the plunger and the cartridge head, wherein the feed-through is connected to a fluid line;
a receptacle for a monomer liquid, wherein the fluid line connects the feed-through to the receptacle in a liquid-permeable manner, wherein the monomer liquid as a second parent component of the bone cement is contained in the receptacle or is fillable or introducible into the receptacle; and
a press-out device pushable into the receptacle, so that monomer liquid is pressable out of the receptacle into the fluid line,
wherein the plunger is spaced from a back side of the cylindrical interior, located opposite the front side, so that, by moving the plunger in the direction of the back side, the press-out device is pushable into the receptacle and a reduced pressure is producible in the interior of the cartridge between the plunger and the cartridge head, and
further wherein:
a mouth for introducing the monomer liquid into the receptacle is arranged in the region of the press-out device, wherein the mouth is closed by pushing in the press-out device when the press-out device begins to move into the receptacle;
the receptacle is arranged on the back side of the cartridge and the plunger pushes the press-out device into the receptacle during movement in the direction of the back side of the cartridge, wherein the region between the press-out device and the plunger is opened towards the outside; or
the receptacle is delimited by a closed hollow cylinder separated from the cartridge and in which a pump plunger as a press-out device is supported to be axially movable, wherein the pump plunger is in circumferential and tight contact with the inner wall of the hollow cylinder, wherein the hollow cylinder is connected to the fluid line at a first lower, base and connected to the interior of the cartridge via a compressed gas line or a hydraulic line on the back side of the cartridge at a second, preferably upper, base, wherein the back side of the cartridge is closed except for the mouth leading into the compressed gas line or the hydraulic line, so that, during movement of the plunger in the direction of the back side of the interior, an overpressure or a pressure is produced in the space between the plunger and the back side, which is passed into the hollow cylinder through the compressed gas line or the hydraulic line.

28. The storage and mixing device according to claim 27, wherein the plunger in the interior of the cartridge is pushable or pullable manually in the direction of the back side of the interior by means of a rod or another force transmission means, wherein an actuating means or a handle for operating the rod or the force transmission means is affixed to the rod or the force transmission means.

29. The storage and mixing device according to claim 27, further comprising:
a porous filter arranged in the cartridge head, in the feed-through and/or in the fluid line, wherein the filter is permeable to the monomer liquid and impermeable to the powdery first parent component.

30. The storage and mixing device according to claim 27, wherein the plunger is spaced from a back side of the cylindrical interior, located opposite the front side, to an extent that the reduced pressure is able to suck the monomer liquid out of the fluid line into the interior of the cartridge.

31. The storage and mixing device according to claim 27, further comprises:
a container separate from the cartridge and from the receptacle and in which the monomer liquid is contained, wherein the container is connected to the receptacle, via an opening, wherein a closed glass ampoule or a foil bag containing the monomer liquid is arranged or is arrangeable in the container, wherein the glass ampoule is breakable open within the container or the foil bag is pierceable open or tearable open within the container.

32. The storage and mixing device according to claim 31, wherein the cartridge, the receptacle, the separate container and the fluid line are connected to a common stand, wherein the receptacle, the container and the fluid line are permanently connected to the stand and the cartridge is releasably connected to the stand, the cartridge being screwed to the stand by means of a thread or connected to the stand by means of a latching mechanism.

33. The storage and mixing device according to claim 31, wherein the foil bag or the glass ampoule is contained in the separate container, which is openable within the separate container, so that the monomer liquid flows out of the opened monomer liquid container into the receptacle, wherein an opening device for opening the monomer liquid container, operable from outside, is arranged on the container.

34. The storage and mixing device according to claim 27, further comprising: a mixing device arranged in the interior of the cartridge between the plunger and the cartridge head, by means of which the first parent component is mixable with the monomer liquid in the interior of the cartridge.

35. The storage and mixing device according to claim 34, wherein the mixing device is operable from outside the cartridge by means of a mixing rod, wherein the mixing rod passes through the cartridge head in a gas-tight manner and is rotatable and movable in the axial direction, the mixing rod passing through the delivery opening.

36. The storage and mixing device according to claim 34, wherein the plunger is pushable in the direction of the back side of the interior of the cartridge by means of the mixing rod.

37. The storage and mixing device according to claim 34, wherein the mixing rod is a delivery pipe in which a manually removable core is arranged, so that the mixed bone cement paste is dischargeable from the interior of the cartridge through the delivery pipe without the core.

38. The storage and mixing device according to claim 27, wherein, inside the interior of the cartridge on the back side, a stop is provided which limits the movement of the plunger in the direction of the back side.

39. The storage and mixing device according to claim 27, wherein the plunger has at least one latching element which is releasably engageable with a complementary latching element on the inner side of the cartridge in the region of the back side of the interior.

40. The storage and mixing device according to claim 27, wherein a closable gaspermeable opening is arranged in the cartridge head, wherein a porous disc which is permeable to gases and impermeable to solid particles is arranged between the first parent component and the opening, wherein the porous disc is arranged in the cartridge head.

41. The storage and mixing device according to claim 27, wherein the plunger is spaced from the press-out device, so that a reduced pressure is first built up in the interior of the cartridge, without the press-out device being moved, when the plunger is moved in the direction of the back side of the cartridge in a first section, and, in addition, the press-out device is pushed into the receptacle when the plunger is moved in a second section.

42. The storage and mixing device according to claim 27, wherein the press-out device is a pump plunger and the receptacle is a hollow cylinder in which the pump plunger is axially movable, wherein an extension, in the form of a cylindrical body, is arranged on the upper side of the pump plunger, which extension has an outer diameter smaller than or equal to the inner diameter of the interior of the cartridge, wherein the pump plunger with the extension is arranged in the hollow cylinder in such a manner that the extension projects into the interior of the cartridge.

* * * * *